US008936556B2

(12) United States Patent
Lee et al.

(10) Patent No.: US 8,936,556 B2
(45) Date of Patent: Jan. 20, 2015

(54) MINUTE VENTILATION-BASED DISORDERED BREATHING DETECTION

(75) Inventors: Kent Lee, Shoreview, MN (US); Yi Zhang, Plymouth, MN (US); Paul F. Emerson, St. Louis Park, MN (US); Jesse W. Hartley, White Bear Lake, MN (US); John D. Hatlestad, Maplewood, MN (US); Jonathan T. Kwok, Holmdel, NJ (US); Weiguang Shao, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 788 days.

(21) Appl. No.: 12/564,741

(22) Filed: Sep. 22, 2009

(65) Prior Publication Data

US 2010/0100000 A1 Apr. 22, 2010

Related U.S. Application Data

(60) Provisional application No. 61/099,705, filed on Sep. 24, 2008.

(51) Int. Cl.
| | |
|---|---|
| *A61B 5/02* | (2006.01) |
| *G06N 5/02* | (2006.01) |
| *A61B 5/08* | (2006.01) |
| *A61B 5/00* | (2006.01) |
| *A61B 5/091* | (2006.01) |
| *A61B 5/04* | (2006.01) |
| *A61B 5/0488* | (2006.01) |
| *A61B 5/0476* | (2006.01) |
| *A61B 5/0402* | (2006.01) |
| *A61B 5/029* | (2006.01) |
| *A61B 5/11* | (2006.01) |

(52) U.S. Cl.
CPC ........... *A61B 5/0809* (2013.01); *A61B 5/04001* (2013.01); *A61B 5/0488* (2013.01); *A61B 5/4818* (2013.01); *A61B 5/0476* (2013.01); *A61B 5/0402* (2013.01); *A61B 5/091* (2013.01); *A61B 5/029* (2013.01); *A61B 5/11* (2013.01)
USPC ............................... 600/538; 706/54; 702/19

(58) Field of Classification Search
USPC .................................. 600/529, 533–536, 538
See application file for complete search history.

(56) References Cited

U.S. PATENT DOCUMENTS

| | | | |
|---|---|---|---|
| 4,365,636 | A | 12/1982 | Barker |
| 4,702,253 | A | 10/1987 | Nappholz et al. |
| 4,827,935 | A | 5/1989 | Geddes et al. |

(Continued)

FOREIGN PATENT DOCUMENTS

| | | |
|---|---|---|
| EP | 1151718 | 11/2001 |
| EP | 1317943 | 6/2003 |
| WO | WO0001438 | 1/2000 |

*Primary Examiner* — Patricia Mallari
*Assistant Examiner* — Michael Catina
(74) *Attorney, Agent, or Firm* — Seager, Tufte & Wickhem, LLC

(57) ABSTRACT

A respiration pattern of a number of respiration cycles is detected and breath intervals (BI) and tidal volume (TVOL) measurements of each of the respiration cycles are respectively determined. An unevenly sampled instantaneous minute ventilation (iMV) signal is produced using the BI and TVOL measurements, and an evenly sampled iMV signal (resampled iMV signal) is produced using the unevenly sampled iMV signal. Disordered breathing is detected based on a comparison between a baseline threshold and the resampled iMV signal.

22 Claims, 14 Drawing Sheets

(56) References Cited

U.S. PATENT DOCUMENTS

| | | | |
|---|---|---|---|
| 4,901,725 A * | 2/1990 | Nappholz et al. ............... 607/17 |
| 5,146,918 A | 9/1992 | Kallok et al. |
| 5,178,156 A | 1/1993 | Takishima et al. |
| 5,233,983 A | 8/1993 | Markowitz |
| 5,335,657 A | 8/1994 | Terry, Jr. et al. |
| 5,487,753 A | 1/1996 | MacCarter et al. |
| 5,496,450 A | 3/1996 | Blumenthal et al. |
| 5,690,687 A | 11/1997 | Hansen |
| 5,792,196 A | 8/1998 | Cooper et al. |
| 5,792,198 A | 8/1998 | Nappholz |
| 5,817,135 A | 10/1998 | Cooper et al. |
| 5,817,136 A | 10/1998 | Nappholz et al. |
| 5,824,020 A | 10/1998 | Cooper |
| 5,836,988 A | 11/1998 | Cooper et al. |
| 5,944,680 A | 8/1999 | Christopherson et al. |
| 5,951,593 A | 9/1999 | Lu et al. |
| 5,964,788 A | 10/1999 | Greenhut |
| 6,064,910 A | 5/2000 | Andersson et al. |
| 6,120,441 A | 9/2000 | Griebel |
| 6,126,611 A | 10/2000 | Bourgeois et al. |
| 6,132,384 A | 10/2000 | Christopherson et al. |
| 6,415,183 B1 | 7/2002 | Scheiner et al. |
| 6,454,719 B1 | 9/2002 | Greenhut |
| 6,572,557 B2 | 6/2003 | Tchou et al. |
| 6,580,944 B1 | 6/2003 | Katz et al. |
| 6,589,188 B1 | 7/2003 | Street et al. |
| 6,741,885 B1 | 5/2004 | Bornzin et al. |
| 6,752,765 B1 | 6/2004 | Strobel et al. |
| 6,752,766 B2 | 6/2004 | Kowallik et al. |
| 6,810,287 B2 | 10/2004 | Zhu et al. |
| 6,881,192 B1 | 4/2005 | Park |
| 6,904,320 B2 * | 6/2005 | Park et al. ...................... 607/17 |
| 6,964,641 B2 | 11/2005 | Cho et al. |
| 7,065,409 B2 | 6/2006 | Mazar |
| 7,127,300 B2 | 10/2006 | Mazar et al. |
| 7,160,252 B2 | 1/2007 | Cho et al. |
| 7,189,204 B2 | 3/2007 | Ni et al. |
| 7,225,013 B2 | 5/2007 | Geva et al. |
| 7,252,640 B2 | 8/2007 | Ni et al. |
| 7,400,928 B2 | 7/2008 | Hatlestad |
| 2003/0163059 A1 | 8/2003 | Poezevera et al. |
| 2004/0006375 A1 * | 1/2004 | Poezevera ...................... 607/17 |
| 2004/0111040 A1 * | 6/2004 | Ni et al. ........................ 600/534 |
| 2004/0128161 A1 | 7/2004 | Mazar et al. |
| 2004/0133079 A1 | 7/2004 | Mazar et al. |
| 2005/0039745 A1 | 2/2005 | Stahmann et al. |
| 2005/0042589 A1 * | 2/2005 | Hatlestad et al. ............. 434/262 |
| 2005/0043652 A1 | 2/2005 | Lovett et al. |
| 2005/0043772 A1 | 2/2005 | Stahmann et al. |
| 2005/0061315 A1 * | 3/2005 | Lee et al. ................. 128/200.24 |
| 2005/0137487 A1 * | 6/2005 | Zhu et al. ...................... 600/513 |
| 2007/0021678 A1 | 1/2007 | Beck et al. |
| 2007/0135725 A1 * | 6/2007 | Hatlestad ...................... 600/529 |
| 2007/0161873 A1 | 7/2007 | Ni et al. |
| 2008/0045815 A1 * | 2/2008 | Derchak et al. ............... 600/301 |

\* cited by examiner

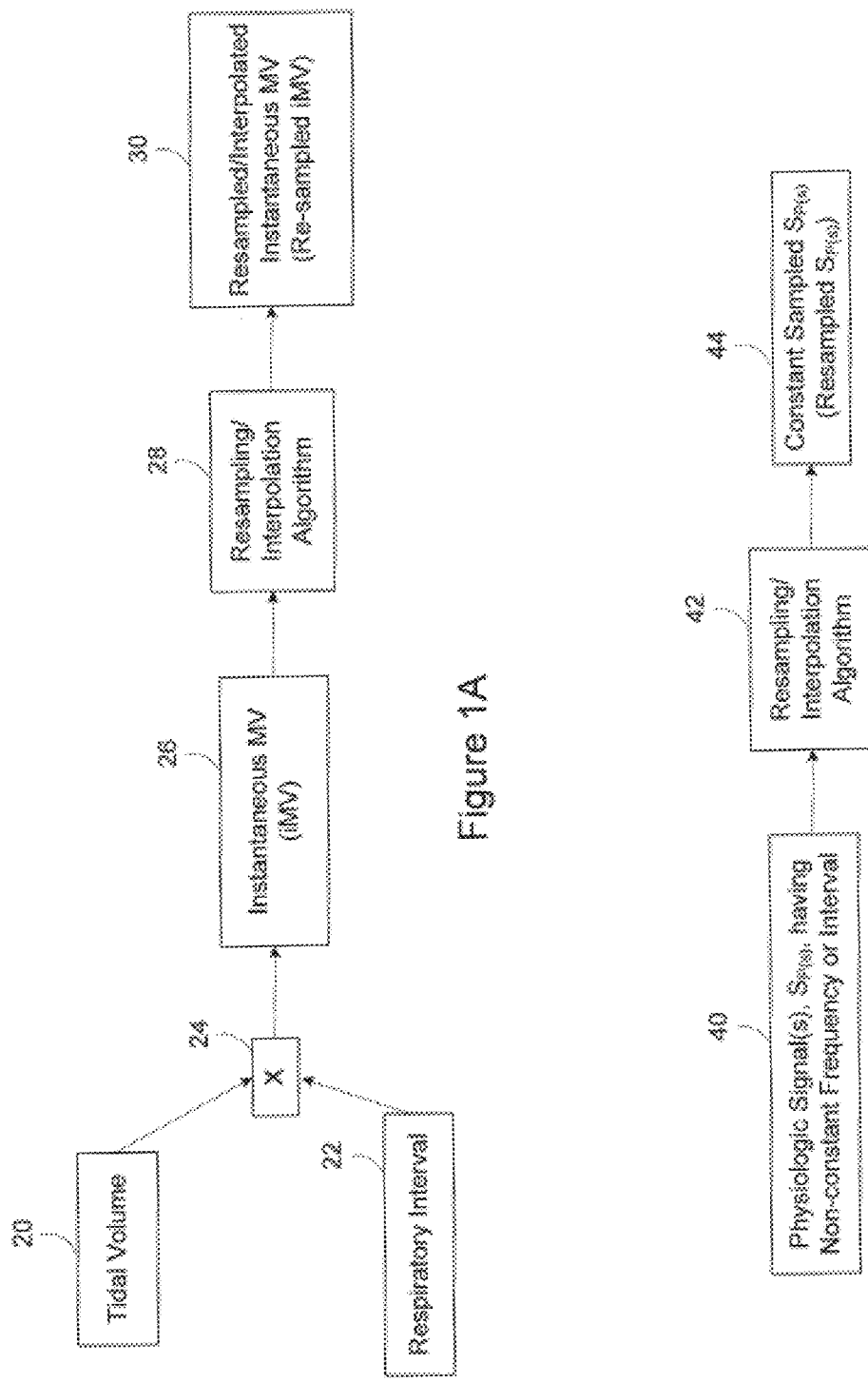

Breath and tidal volume detection

Instantaneous minute ventilation $Value_k = (prev\ sample\ interval + next\ sample\ interval) / I_1$

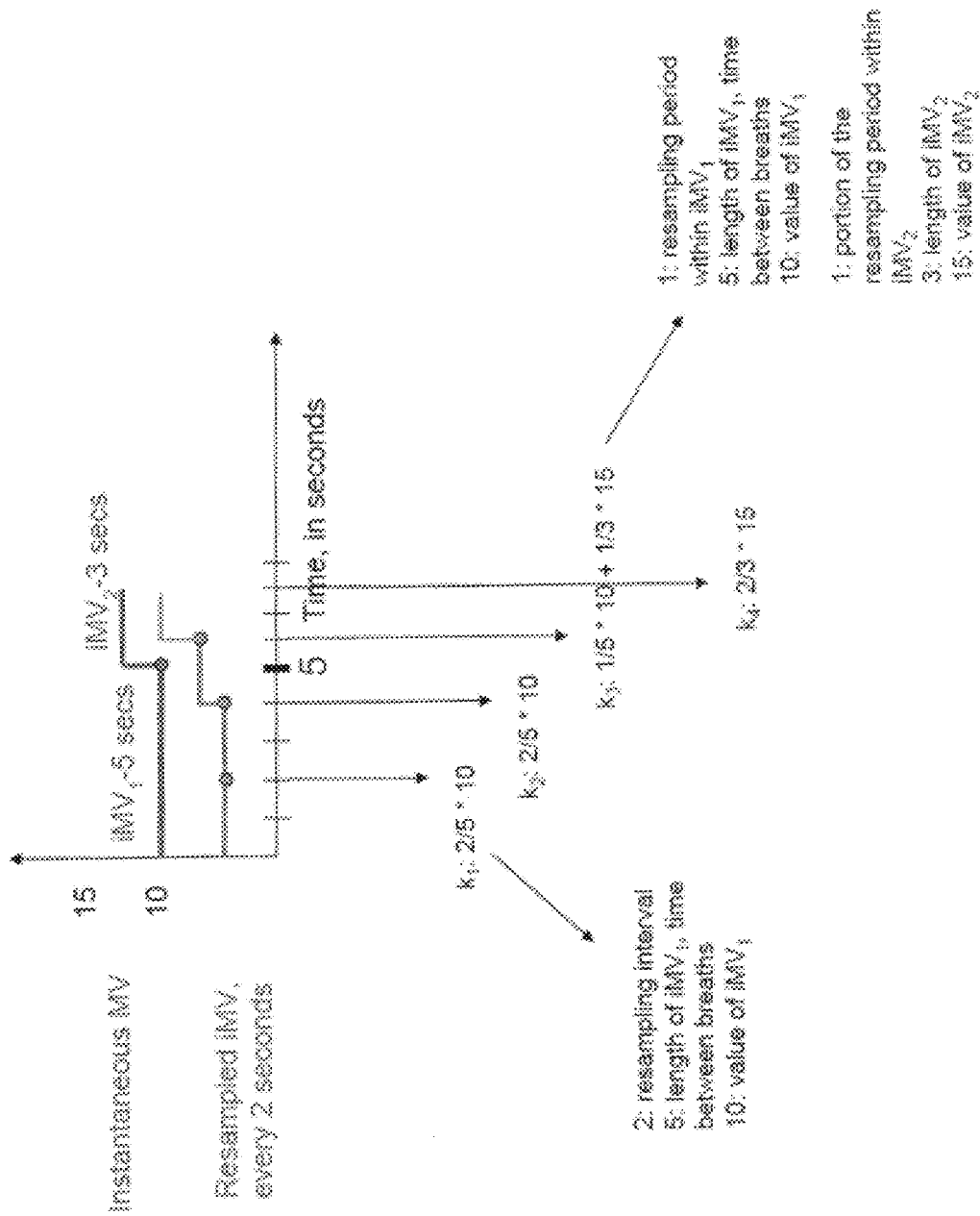

MINUTE VENTILATION-BASED DISORDERED BREATHING DETECTION

RELATED APPLICATIONS

This application claims the benefit of Provisional Patent Application Ser. No. 61/099,705, filed on Sep. 24, 2008, to which priority is claimed pursuant to 35 U.S.C. §119(e) and which is hereby incorporated herein by reference.

FIELD OF THE INVENTION

The present invention relates generally to detecting disordered breathing using a minute ventilation-based detection methodology.

BACKGROUND OF THE INVENTION

Sleep is generally beneficial and restorative to a patient, exerting great influence on the quality of life. A typical night's sleep for a normal person begins with a sleep stage known as slow wave sleep (SWS) characterized by low frequency electroencephalogram (EEG) activity. As the person falls asleep, brain activity declines and there is a progressive increase in the depth of sleep. At approximately ninety minute intervals, sleep lightens and a sleep stage known as rapid eye movement (REM) sleep is initiated. REM sleep is characterized by high frequency EEG activity, bursts of rapid eye movements, skeletal muscle atonia, and heightened autonomic activity.

There are typically 4-6 REM periods per night, with increasing duration and intensity toward morning. While dreams can occur during either REM or SWS sleep, the nature of the dreams varies depending on the type of sleep. REM sleep dreams tend to be more vivid and emotionally intense than SWS sleep dreams. Furthermore, autonomic nervous system activity is dramatically altered when REM sleep is initiated.

In patients with respiratory or heart disease, the brain during sleep can precipitate breathing disturbances, myocardial ischemia, or arrhythmia. Although REM sleep is a necessary component of normal sleep, serious consequences may be associated with both the increase in autonomic activity and the intense emotional responses that accompany dreaming in patients with cardiovascular disease or respiratory disorders, for example.

Disruptions of the respiratory system during sleep may include the conditions of sleep apnea or sleep hypopnea. Sleep apnea is a serious breathing disorder caused by airway obstruction, denoted obstructive sleep apnea, or derangement in central nervous system control of respiration, denoted central sleep apnea. Regardless of the type of apnea, people with sleep apnea stop breathing repeatedly during their sleep, sometimes hundreds of times a night and sometimes for a minute or longer. Whereas sleep apnea refers to cessation of breathing, hypopnea is associated with periods of abnormally slow or shallow breathing. With each apnea or hypopnea event, the person generally briefly arouses to resume normal breathing. As a result, people with sleep apnea or hypopnea may experience sleep fragmented by frequent arousals.

An adequate quality and quantity of sleep is required to maintain physiological homeostasis. Prolonged sleep deprivation or periods of highly fragmented sleep ultimately will have serious health consequences. Chronic lack of sleep may be associated with various cardiac or respiratory disorders affecting a patient's health and quality of life.

SUMMARY OF THE INVENTION

Embodiments of the present invention involve detecting disordered breathing, including apnea and hypopnea, using minute ventilation. Embodiments of the present invention are directed to methods for detecting disordered breathing implemented at least in part within a patient. Methods of the invention involve detecting a respiration pattern of a number of respiration cycles and determining breath intervals (BI) and tidal volume (TVOL) measurements of each of the respiration cycles. Methods of the invention further involve producing an unevenly sampled instantaneous minute ventilation (iMV) signal using the BI and TVOL measurements, and producing an evenly sampled iMV signal (resampled iMV signal) using the unevenly sampled iMV signal. Disordered breathing is detected based on a comparison between a baseline threshold and the resampled iMV signal.

Other embodiments are directed to devices for detecting disordered breathing at least in part within a patient. Devices of the invention include an implantable housing and a sensor system disposed in the housing and configured to detect a respiration pattern of a number of respiration cycles. A processor is coupled to the sensor system. The processor is configured to execute program instructions to determine breath intervals (BI) and tidal volume (TVOL) measurements of each of the respiration cycles, produce an unevenly sampled instantaneous minute ventilation (iMV) signal using the BI and TVOL measurements, produce an evenly sampled iMV signal (resampled iMV signal) using the unevenly sampled iMV signal, and detect disordered breathing based on a comparison between a baseline threshold and the resampled iMV signal.

According to other embodiments, devices for detecting disordered breathing are implemented at least in part within a patient and include a sensor configured to detect a respiration pattern of a number of respiration cycles and circuitry for determining breath intervals (BI) and tidal volume (TVOL) measurements of each of the respiration cycles. Devices of the invention further include means for producing an unevenly sampled instantaneous minute ventilation (iMV) signal using the BI and TVOL measurements, means for producing an evenly sampled iMV signal (resampled iMV signal) using the unevenly sampled iMV signal, and a detector configured to detect disordered breathing based on a comparison between a baseline threshold and the resampled iMV signal.

Some embodiments involve determining if each respiration cycle meets predetermined quality criteria for calculating iMV, and producing, only for each respiration cycle that meets the predetermined quality criteria for purposes of detecting disordered breathing, an iMV signal and a resampled iMV signal. The predetermined quality criteria may include a breathing interval quality criterion based on the breathing interval of a current breath and the breathing interval of at least a previous breath, and the tidal volume of at least one previous breath. The baseline threshold is preferably calculated using only breaths that meet the predetermined quality criteria and disordered breathing is preferably detected using only breaths that meet the predetermined quality criteria.

According to various embodiments, a respiration cycle quality check methodology of the present invention, such as a mid-term baseline (MTBL) approach discussed hereinbelow, may be used for implementing minute ventilation-based disordered breathing detection that does not utilize resampling of an iMV signal. For example, some embodiments involve determining if each respiration cycle meets predetermined quality criteria for calculating iMV and producing, only for each respiration cycle that meets the predetermined quality criteria for purposes of detecting disordered breathing, an iMV signal. Disordered breathing is detected based on a comparison between a baseline threshold and the iMV signal. The baseline threshold is preferably calculated using only breaths that meet the predetermined quality criteria and disordered breathing is preferably detected using only breaths that meet the predetermined quality criteria.

Some embodiments involve computing an Apnea/Hypopnea Index (AHI), which provides a measurement of apnea severity. According to such embodiments, a baseline average iMV value is computed using iMV values measured over a given time period. Periods of apnea and hypopnea are detected when the iMV value is less than the baseline for a pre-determined period of time. The number of detected apnea and hypopnea events are then summed together and divided by total sleep time to derive an AHI value.

According to various embodiments, a methodology for computing a patient's AHI utilizes minute ventilation for purposes of performing respiration cycle quality check computations, such as those implemented by the MTBL approach discussed hereinbelow, and utilizes TVOL for disordered breathing detection, such as apnea/hypopnea detection.

Moreover, a respiration cycle quality check methodology of the present invention may be implemented in a variety of respiratory diagnostics. For example, a respiration rate tracking diagnostic or other respiratory diagnostic may be implemented that utilizes a respiration cycle quality check approach of the present invention, such as the MTBL approach discussed hereinbelow. A respiration cycle quality check methodology of the present invention may be utilized alone or in combination with other advantageous features described herein.

According to other embodiments, a resampling algorithm of the present invention may be implemented to process a wide variety of physiologic signals that are unevenly sampled or aperiodic in nature. Examples of such signals include electrocardiogram (ECG), electrogram (EGM), heart rate variability (HRV), transthoracic impedance, plural pressure, chest wall movement, diaphragm movement, heart rate, blood pressure, blood perfusion, blood gas concentration (e.g., $O_2$ saturation), and nerve traffic indicative of another aperiodic physiologic parameter, among others. A resampling approach of the present invention may be implemented for processing a wide variety of aperiodic physiologic signals for a variety of applications, including monitoring, diagnostics, and therapy applications. A resampling algorithm of the present invention may be utilized alone or in combination with other advantageous features described herein.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIG. 1A is a block diagram showing various elements for producing instantaneous minute ventilation and resampled iMV in accordance with embodiments of the invention;

FIG. 1B is a block diagram showing various elements for processing any type of unevenly sampled physiologic signal and producing an evenly sampled physiologic signal using the unevenly sampled physiologic signal in accordance with embodiments of the invention;

FIG. 14 is a graphical depiction of an algorithm that provides for resampling of an iMV signal every 2 seconds in accordance with embodiments of the invention.

Figure 2A:
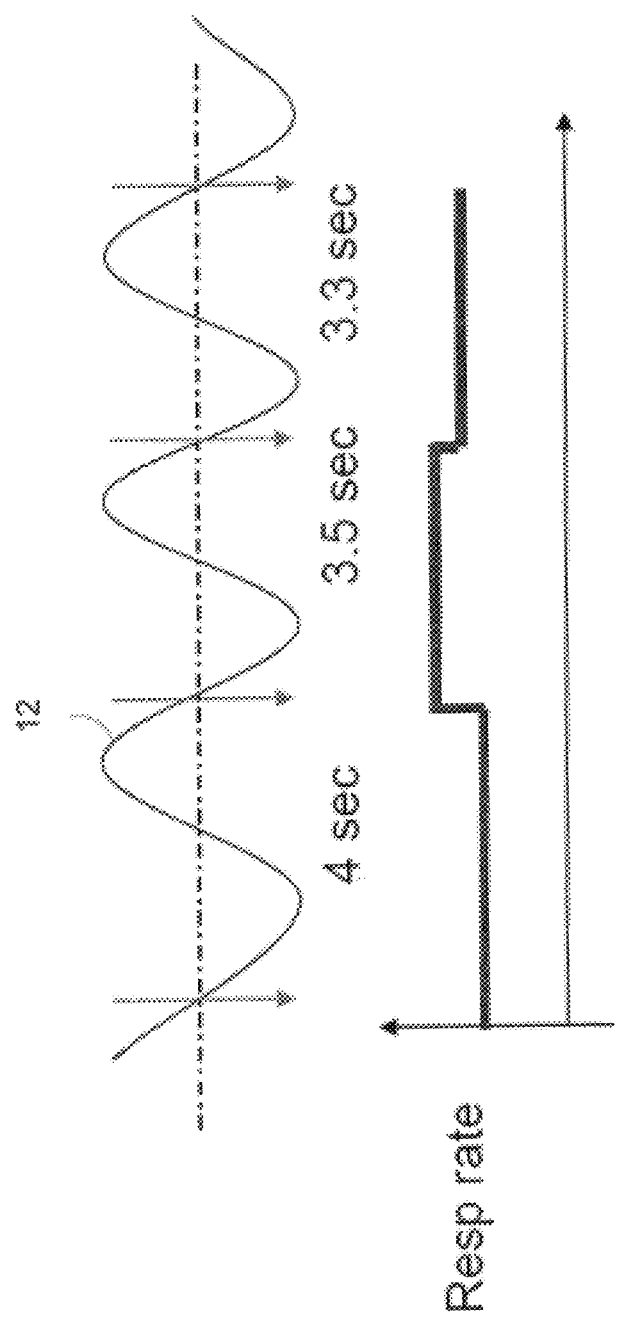
FIG. 2A is a graph of an unevenly sampled transthoracic impedance signal (and corresponding uneven respiration rate signal) that may be processed to produce an instantaneous tidal volume signal, an evenly sampled instantaneous tidal volume signal, an iMV signal, and a resampled iMV signal in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

A wide variety of medical devices may be configured to detect disordered breathing using a minute ventilation-based methodology in accordance with the present invention. Such devices may be configured with a variety of sensor arrangements for sensing patient respiration from which minute ventilation can be calculated, including respiration sensors, implantable intrathoracic respiration sensors, such as transvenous, endocardial, and/or epicardial sensors (i.e., intrathoracic electrodes), and/or subcutaneous, non-intrathoracic sensors, including can, header, and indifferent electrodes, and subcutaneous arrays or lead electrodes (i.e., non-intrathoracic electrodes).

An adequate duration and quality of sleep is required to maintain physiological homeostasis. Prolonged sleep deprivation or periods of poor quality sleep ultimately will have serious health consequences. Disordered breathing, such as sleep apnea and hypopnea, is a major cause of interrupted sleep. People suffering from sleep apnea repeatedly stop breathing during sleep. Hypopnea is a related condition, characterized by periods of abnormally slow or shallow breathing.

Sleep apnea/hypopnea may be obstructive, central, or a mixture of the two types. Obstructive sleep apnea/hypopnea is the most common type and is typically caused by a blockage of the airway, usually when the soft tissue in the throat collapses and closes during sleep. In central sleep apnea/hypopnea, the airway is not blocked but there is an interruption in signals from the brain controlling breathing. With each apnea/hypopnea event, the person may briefly arouse in order to resume breathing. The frequent interruptions during sleep result in extremely fragmented sleep of poor quality. Untreated, sleep apnea/hypopnea has a number of adverse health and quality of life consequences ranging from high blood pressure and other cardiovascular diseases to memory problems, headaches and degradation of social and work related activities.

Diagnosis of the conditions causing sleep disturbances, including disordered breathing, may require people suffering from sleep disorders to spend one or more nights in a sleep laboratory. In the sleep laboratory setting, a patient can be instrumented for data acquisition and observed by trained personnel. Polysomnography may be used to diagnose and determine the severity of sleep apnea/hypopnea. During this procedure, a variety of physiological functions are externally detected and recorded during sleep, such as the electrical activity in the brain, eye movement, muscle activity, heart rate, respiratory effort, and blood oxygen levels. Manual evaluation of these physiological functions is performed by a technician and used to diagnose disordered breathing such as sleep apnea/hypopnea and assess possible therapeutic interventions.

Testing in a sleep laboratory setting presents a number of obstacles in acquiring an accurate picture of a patient's typical sleep patterns. For example, spending a night in a laboratory typically causes a patient to experience a condition known as "first night syndrome," involving disrupted sleep during the first few nights in an unfamiliar location. Furthermore, sleeping while instrumented and observed may not result in a realistic perspective of the patient's normal sleep patterns.

Various embodiments of the invention involve detecting disordered breathing preferably based on sensed signals indicative of tidal volume (TVOL) and breath interval (BI). Sensed signals indicative of tidal volume and breath interval are preferably processed to produce a minute ventilation (MV) signal which has a unique character relative to a conventional MV signal and is used for disordered breathing detection. In some embodiments, an MV signal is used for the dual purpose of determining that the patient is asleep and detecting disordered breathing while the patient is asleep. In one approach, a conventional MV signal is used to determine that the patient is asleep, and a non-conventional MV signal produced in accordance with the present invention is used to detect disordered breathing. In another approach, a non-conventional MV signal produced in accordance with the present invention is used both to determine that the patient is asleep and to detect disordered breathing.

In general, minute ventilation is computed as the product of TVOL and respiration rate. An MV signal in accordance with embodiments of the present invention is preferably generated using TVOL and BI signal information on a breath-to-breath basis. More particularly, and as shown in FIG. 1A, an instantaneous MV signal (iMV) 26 is generated using the product 24 of the instantaneous TVOL (iTVOL) 20 and the breath or respiratory interval, BI 22.

The iMV signal 26 may be subject to processing by a resampling or interpolation algorithm 28 to produce a uniformly sampled iMV signal 30, referred to as a resampled or interpolated iMV signal 30.

Respiratory signals, such as TVOL, MV, BI and iMV, are considered unevenly sampled signals. Sampling does not occur at a constant frequency or interval for these and other physiologic signals, such as ECG, EGM, HRV signals, for example. Rather, sampling occurs in concert with the physiological event or process from which the physiologic signal is derived (such events or processes being aperiodic). In the case of respiratory signals 12, an example of which is shown in FIG. 2A, sampling occurs whenever a breath occurs (i.e., the physiologic event/process in this case includes expiration and inspiration). A respiration rate associated with the respiratory signal 12 is, therefore, also non-periodic or unevenly sampled.

Information about the original physiologic signal, such as a respiratory signal, is not lost when using a resampling method of the present invention. Once a uniformly sampled signal has been determined, it can be filtered with standard filtering techniques (e.g., IIR, FIR, etc). Without a constant sampling rate, filter coefficients cannot be determined. This resampling methodology is particularly well suited for apnea and hypopnea detection, and background averages can be calculated from the resampled signal.

The respiration frequency is variable, especially during periods of apnea, and the "respiratory interval" cannot be computed until the next breath occurs. This presents a problem in the case of disordered breathing detection. For apnea detection, by way of example, a large single-point drop should result in the MV signal when an apnea event occurs, which corresponds to the patient's temporary cessation of breathing. However, conventional apnea detection approaches typically use large averaging windows to produce an MV signal, which reduces detection resolution of fast changes in patient breathing patterns, such as those associated with apnea and hypopnea events. Uniform sampling (interpolation) according to the present invention solves this problem by interpolating the breath-by-breath instantaneous MV into a consistently sampled signal.

According to various non-limiting embodiments, uniformly sampled signed transthoracic impedance measurements are used to detect breaths. When the signal passes a predetermined negative level (hysteresis) and subsequently passes a predetermined positive level (hysteresis), a breath is declared detected on the subsequent zero cross. The time between zero crosses defines the breath interval (BI) and the difference between the maximal impedance and minimal impedance between these two zero crosses defines the tidal volume (TV). These breath intervals are non-uniform and the instantaneous minute ventilation (TV*60/BI) is based on non-uniform data. The resampling procedure according to embodiments of the present invention contemplates determining an instantaneous minute ventilation based on uniform intervals. It is understood that breath detection may be accomplished using a variety of techniques, such as detecting the positive zero crossing or detecting peaks, among others.

An advantage of using a uniformly or constant sampled iMV signal concerns enabling filtering of non-uniformly sampled MV signals without resorting to large averaging windows. Another advantage concerns the ability to use any respiration signal or surrogate respiration signal (e.g., electrocardiogram, electrogram, pressure, heart rate variability). Use of a constant sampled iMV signal enables more accurate respiration diagnostics. For example, use of a constant sampled iMV signal produced in accordance with the present invention allows for more precise determination of minute ventilation without using the entire respiratory signal.

Previous approaches for detecting disordered breathing have used the tidal volume amplitude to detect periods of apnea and hypopnea. Conventional tidal volume-based algorithms make gross assumptions about the sampling rate which are not always correct, especially during periods of apnea and hyperventilation. It has been found that use of a tidal volume signal, when used alone for purposes of disordered breathing detection, can lead to increased false detections, primarily due to the limited sensitivity and specificity of TVOL-only disordered breathing detection techniques and tidal volume-based signal detection techniques. The frequency of false detection of disordered breathing has been found to increase for mild forms of disordered breathing (i.e., border events), thereby resulting in reduced detection resolution.

A disordered breathing detection approach of the present invention uses respiratory interval information (e.g., breath interval data) in combination with tidal volume data to generate instantaneous MV data and resampled iMV signals, which can provide for enhanced sensitivity and specificity for detecting disordered breathing, such as apnea and hypopnea, and discriminating between types of disordered breathing (e.g., apnea distinguished from hypopnea).

An instantaneous MV signal and a resampled iMV signal produced and used in accordance with the present invention have been found to be more sensitive to periods of apnea than a TVOL signal, for example, due to decreased tidal volumes and lower respiratory rates associated with apnea. It is understood that decreased tidal volumes associated with apnea episodes results in TVOL signal amplitudes of reduced amplitude (e.g., reduced to near DC during cessation of breathing during an apnea event), which correspondingly reduces the sensitivity of an apnea or other disordered breathing detection scheme that relies solely on a TVOL signal. Hyperventilation that occurs after apnea, for example, results in increased tidal volumes and respiratory rates. Respiratory interval information of an instantaneous MV signal is used to compliment TVOL information of the MV signal to provide for enhanced resolution of hyperventilation detection and detection of transitions between apnea, hypopnea, hyperventilation, and normal breathing states.

As is shown in FIG. 1B, the processes of FIG. 1A can be generalized and utilized for processing any aperiodic physiologic signal that is unevenly sampled. Such signals include ECG, EGM, HRV, transthoracic impedance, plural pressure, chest wall movement, diaphragm movement, heart rate, blood pressure, blood perfusion, blood gas concentration (e.g., $O_2$ saturation), and nerve traffic indicative of another aperiodic physiologic parameter, among others. In FIG. 1B, one or more physiologic signals, $S_{P(s)}$, are acquired or received 40 and subject to a resampling/interpolation algorithm 42. This algorithm 42 produces constant sampled physiologic signals, $S_{P(s)}$ 44 (i.e., resampled $S_{P(s)}$). One skilled in the art will readily appreciate the advantages of implementing a resampling approach of the present invention for processing a wide variety of aperiodic physiologic signals for a variety of applications, including monitoring, diagnostics, and therapy applications. It is noted that, in some approaches, averaging filters, which provide relatively consistent performance due to a constant sampling rate, may be used to produce a uniformly sampled iMV signal.

Figure 2B:
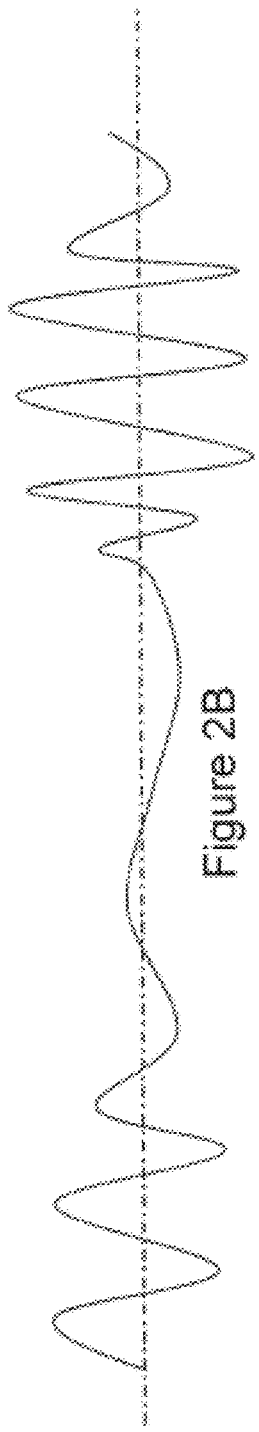
FIGS. 2B-2D facilitate an understanding of an iMV signal generation approach in accordance with embodiments of the present invention.
Figure 2C:
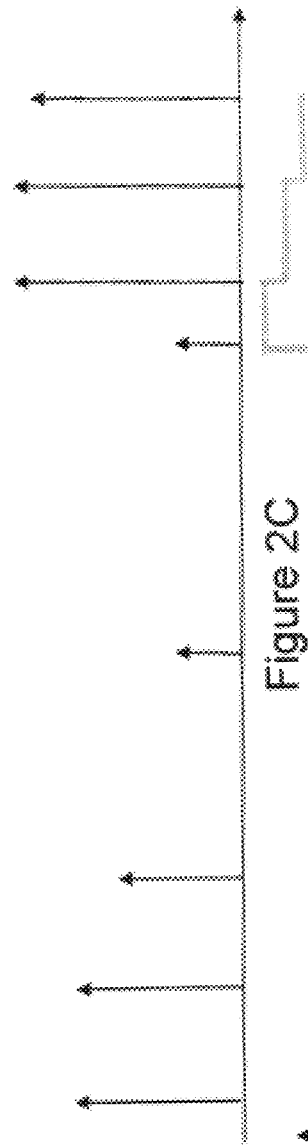
Figure 2D:
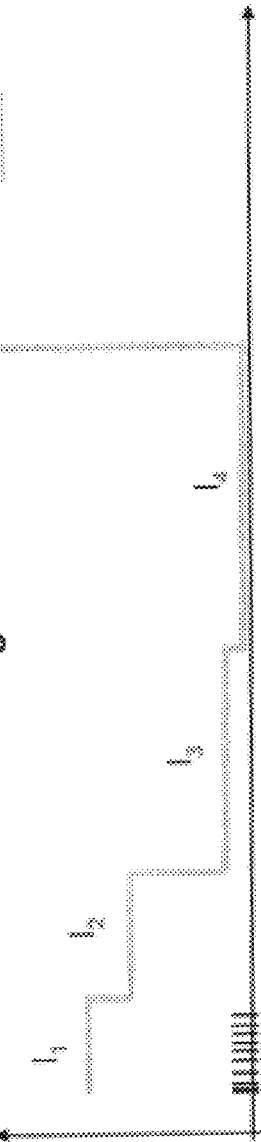

According to various embodiments, an MV signal is processed in a manner that produces an instantaneous MV or iMV signal. FIGS. 2B-2D facilitate an understanding of an iMV signal generation approach in accordance with embodiments of the present invention. A respiration waveform is shown in FIG. 2B, which evidences an apnea event. FIG. 2C shows markers that indicate both time and magnitude corresponding to detection of breaths (breath interval) and tidal volume based on the respiration waveform of FIG. 2B. FIG. 2D shows a plot of an instantaneous minute ventilation signal derived from the breath interval and tidal volume data shown in FIG. 2C.

For each breath interval ($I_1$-$I_N$), iMV is calculated, such as by using the following algorithm:

Within breath interval $I_1$:

resampled iMV$_1$=(resampling interval/$I_1$)*TV($I_1$)*RR($I_1$)

If a new breath $I_2$ falls between resampling intervals: then use a weighted average Resampled iMV$_2$=(($I_1$-iMV-sample-time$_{previous}$)/$I_1$) *TV($I_1$)*RR($I_1$)+(($I_2$-resampling interval)/$I_2$) *TV($I_2$)*MV($I_2$)

where, TV and RR are tidal volume and respiration rate, respectively. A resampling algorithm according to one implementation works by determining the percentage of the current interval covered by the new resampling frequency. If the resampling interval falls between two breath intervals, then the resampled value is calculated as a percentage of the first and the percentage of the second interval.

The instantaneous iMV interval is preferably set by choosing the frequency of the resampled signal (e.g., for 2 Hz, a sample is calculated every 0.5 seconds). Within any breath interval, the resampled value is equal the number of seconds between re-sampling (e.g., 0.5 seconds) divided by the total length (in seconds) of the instantaneous signal multiplied by the instantaneous MV value. If the sample falls between two instantaneous values, the weighted average of both is used (e.g., a weighted average of the instantaneous MV signal). A graphical depiction of the algorithm discussed above for resampling iMV every 2 seconds is shown in FIG. 14.

By way of further example, assume an MV signal is determined for each of a breath interval of 3 seconds, a next breath interval of 5 seconds, and following breath interval of 3.5 seconds. A resampling/interpolating algorithm of the present invention converts this non-uniform MV signal to a uniform MV signal that is consistently 0.5 seconds (for example) between samples, and helps smooth the transitions between each breath. This approach also solves the aforementioned conventional apnea detection problem where no breaths are present for 10 seconds, for example, so during the period of no breathing, the MV value using conventional approaches would slowly drift to zero.

According to another non-limiting illustrative example, it is assumed that two breath intervals of 2 seconds and 4 seconds with TV's of 50 ml and 75 ml are found. The associated minute ventilation is 30*50 (1500 ml/minute) and 15*75 (1125 ml/minute). The minute ventilation may be resampled at uniform 3 second intervals, for example, using a weighted average, so at 3 seconds the minute ventilation is ⅔*1500+ ⅓*1125 and at 6 seconds the minute ventilation is ⅔*1125. The baseline values are then computed using these uniform instantaneous values, rather than non-uniform instantaneous values.

In apnea detection approaches that utilize an iMV and/or resampled iMV signal produced in accordance with the present invention, as is illustrated in FIG. 2D, cessation of patient breathing is detected as a sudden drop in the iMV or resampled iMV signal magnitude, and resumption of patient breathing is detected as a sudden increase in the iMV or resampled iMV signal magnitude.

Figure 3:
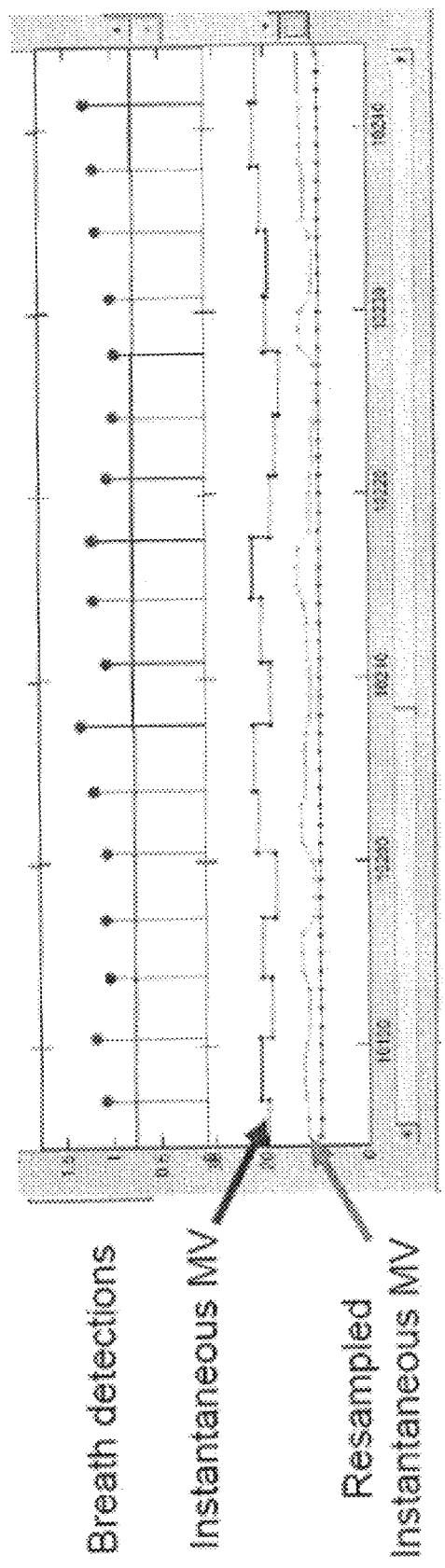
FIG. 3 illustrates a display of various respiratory-related waveforms for a particular patient, including breath detection markers, an iMV signal, and a resampled iMV signal developed in accordance with embodiments of the present invention.

FIG. 3 illustrates a display of various respiratory-related waveforms for a particular patient. In particular, the three display panels depict breath detection markers, an iMV signal developed in a manner discussed herein, and a resampled iMV signal also developed in a manner discussed herein.

Disordered breathing detection according to embodiments of the present invention has been shown to be more impervious to noise from tidal volume fluctuations when compared to conventional approaches. In accordance with various embodiments, apnea, hypopnea, and other forms of disordered breathing are detected using an MV signal derived from signals produced by a transthoracic impedance sensor and processed in accordance with techniques of the present invention. In other embodiments, an MV signal derived from signals produced by an inter-thoracic pressure sensor may be processed in accordance with techniques of the present invention to detect apnea, hypopnea, and other forms of disordered breathing. In particular, apnea and hypopnea are detected using iMV values, such as iMV values derived from a resampled iMV signal.

According to an exemplary embodiment, a baseline average iMV value is computed using iMV values measured over a given time period, such as approximately 120 seconds. Periods of apnea and hypopnea are detected when the iMV value (or a short-term average of the iMV value) is less than the baseline for a pre-determined period of time. The number of detected apnea and hypopnea events are then summed together and divided by total sleep time to derive an Apnea/Hypopnea Index, which provides a measurement of apnea severity.

This process may be enhanced by using a resampled iMV values to establish a baseline average resampled iMV value, and detecting periods of apnea and hypopnea the resampled iMV value (or a short-term average of the resampled iMV value) is less than the baseline for a pre-determined period of time. It has been found that use of iMV signals and resampled iMV signals for disordered breathing detection in accordance with embodiments of the present invention provide for enhanced detection of disordered breathing events relative to conventional disordered breathing detection techniques.

According some approaches, the MV signal is subject to a quality check to provide for enhanced detection of disordered breathing. A quality check is preferably performed for each detected breath, and only qualifying breaths are used for baseline calculations and apnea/hypopnea detection. It has been demonstrated that embodiments employing an MV signal quality check (which may be an optional feature) produce disordered breathing detection results that are nearly or substantially equivalent to detection results obtained using "gold standard" external sensing techniques in a sleep laboratory. When the MV signal quality check is not employed, disordered detection results are at least equivalent and generally better than those obtained using traditional approaches that solely use tidal volume, it being understood that use of an MV signal provides additional benefits, such as sensing patient sleep state, patient activity sensing for rate responsive pacing, among others.

According to one approach, checking MV signal quality involves an average MV value which is computed using a short-term average MV signal value (e.g., sum of the tidal volumes within an 8 second block) and a long-term moving average MV signal value (e.g., based on a weighted average of the long-term moving average MV signal value and the new short-term average MV signal value). This average MV value is compared to a threshold, and if lower than the threshold, then the MV values are low, such that the respiratory sensing device cannot detect breaths properly and thus any calculation on breath tidal volume or interval detection will be erroneous. It is noted that this approach of determining short- and long-term moving average MV signal values for purposes of performing an MV signal quality check is based on an estimate of minute ventilation by summing a number of breaths over a predetermined block of time, while the disclosed approaches to determining iMV and resampled iMV values involve instantaneous multiplication of breath interval and tidal volume.

Some embodiments of the invention involve determining that the patient is asleep, sensing tidal TVOL and BI signals indicative of disordered breathing, computing iMV, and detecting disordered breathing based on the computed iMV (or resampled iMV) relative to a baseline or threshold developed for the patient. Methods of sleep detection are described in commonly owned U.S. Pat. Nos. 7,189,204 and 7,252,640, which are hereby incorporated herein by reference.

Figure 4:
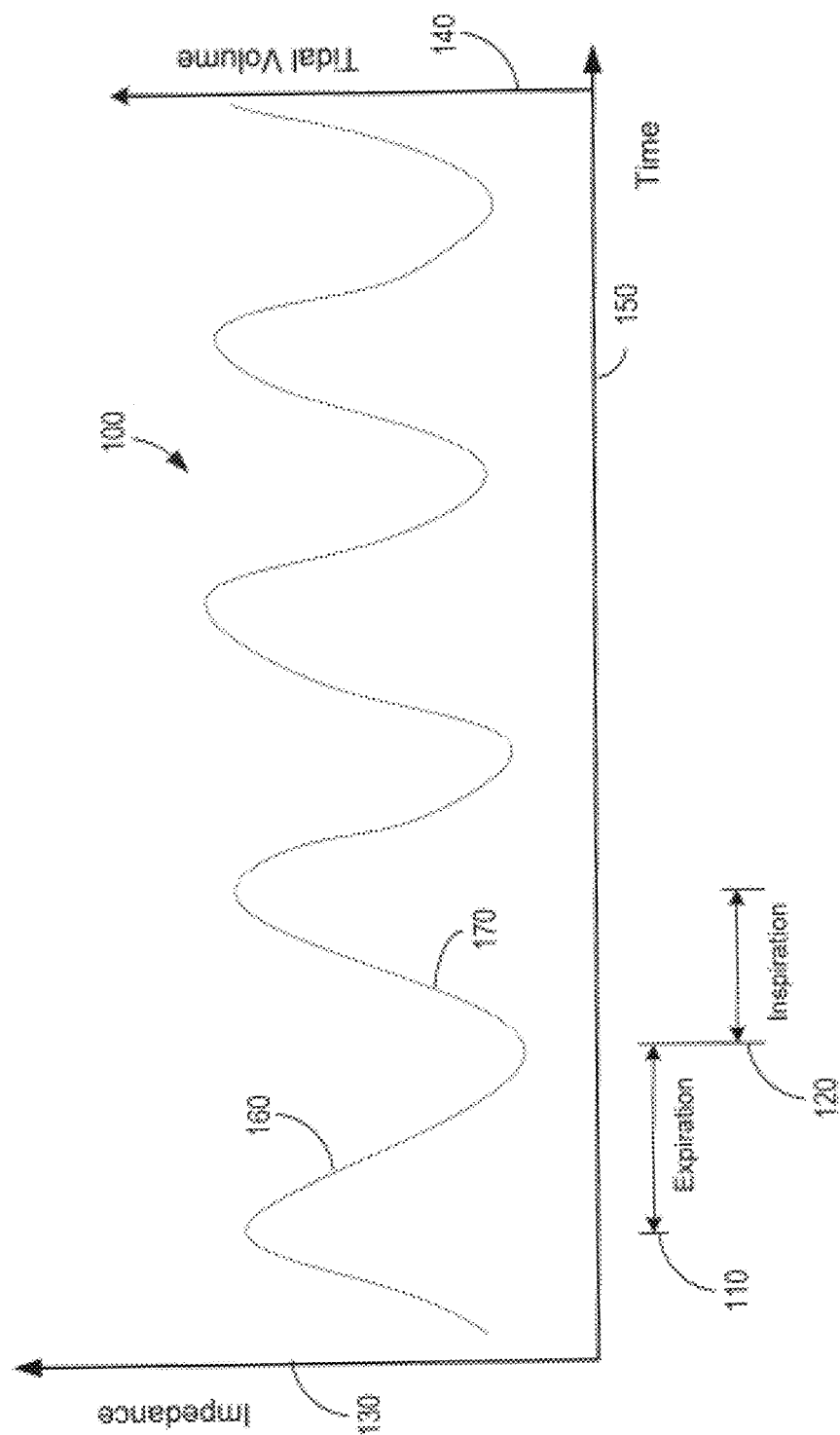
FIGS. 4 and 5 are respiratory waveforms that may be developed by a medical device implementing disordered breathing detection methodologies of the present invention.
Figure 5:
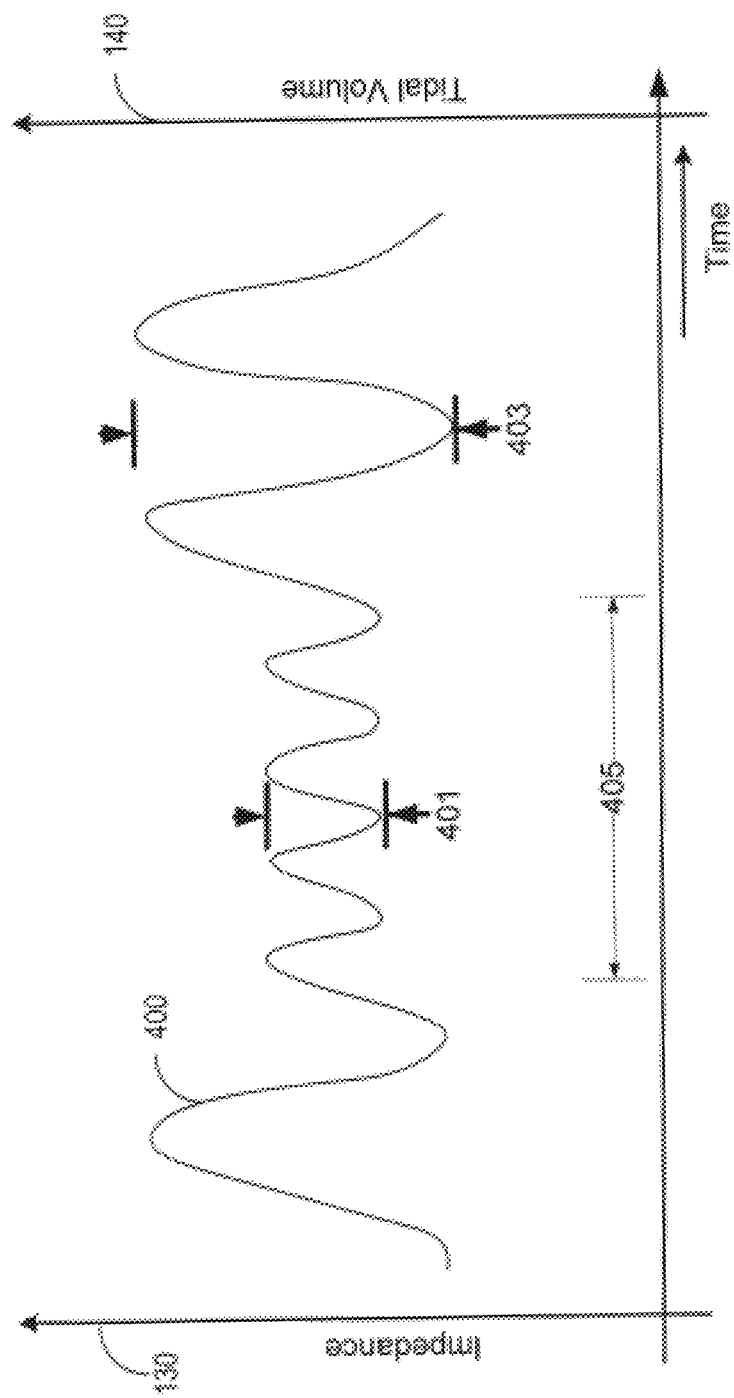

FIG. 4 is a graph of a transthoracic impedance signal 100 that is preferably used in connection with disordered breathing detection according to embodiments of the present invention. An implantable medical device of the present invention employs two or more impedance electrodes that are used to sense variations in a transthoracic impedance signal resulting from patient respiration. For example, the impedance signal 100 may be developed from an impedance sense electrode in combination with a cardiac rhythm management (CRM) device. The impedance voltage signal 100 shown in FIG. 4 is proportional to the transthoracic impedance, with the impedance increasing during respiratory inspiration and decreasing during respiratory expiration. The peak-to-peak transition of the impedance measurement is proportional to the amount of air inhaled in one breath, denoted the tidal volume, also illustrated in FIG. 4.

The impedance of signal 100 increases 170 during any respiratory inspiration 120 and decreases 160 during any respiratory expiration 110. The impedance signal 100 is also proportional to the amount of air inhaled, denoted by a tidal volume 140, illustrated on the abscissa of the right side of the graph in FIG. 4. The variations in impedance during respiration, identifiable as the peak-to-peak variation of the impedance signal 100, may be used to determine the respiration tidal volume 140. Tidal volume 140 corresponds to the volume of air moved in a breath, one cycle of expiration 110 and inspiration 120. An instantaneous MV signal is generated using the product of the instantaneous TVOL and the breath interval derived from the impedance signal 100 as previously discussed. The iMV signal may be further processed to produce a resampled iMV signal, such as in the manner previously described and as shown in FIGS. 1A, 1F, and 3.

Figure 8:
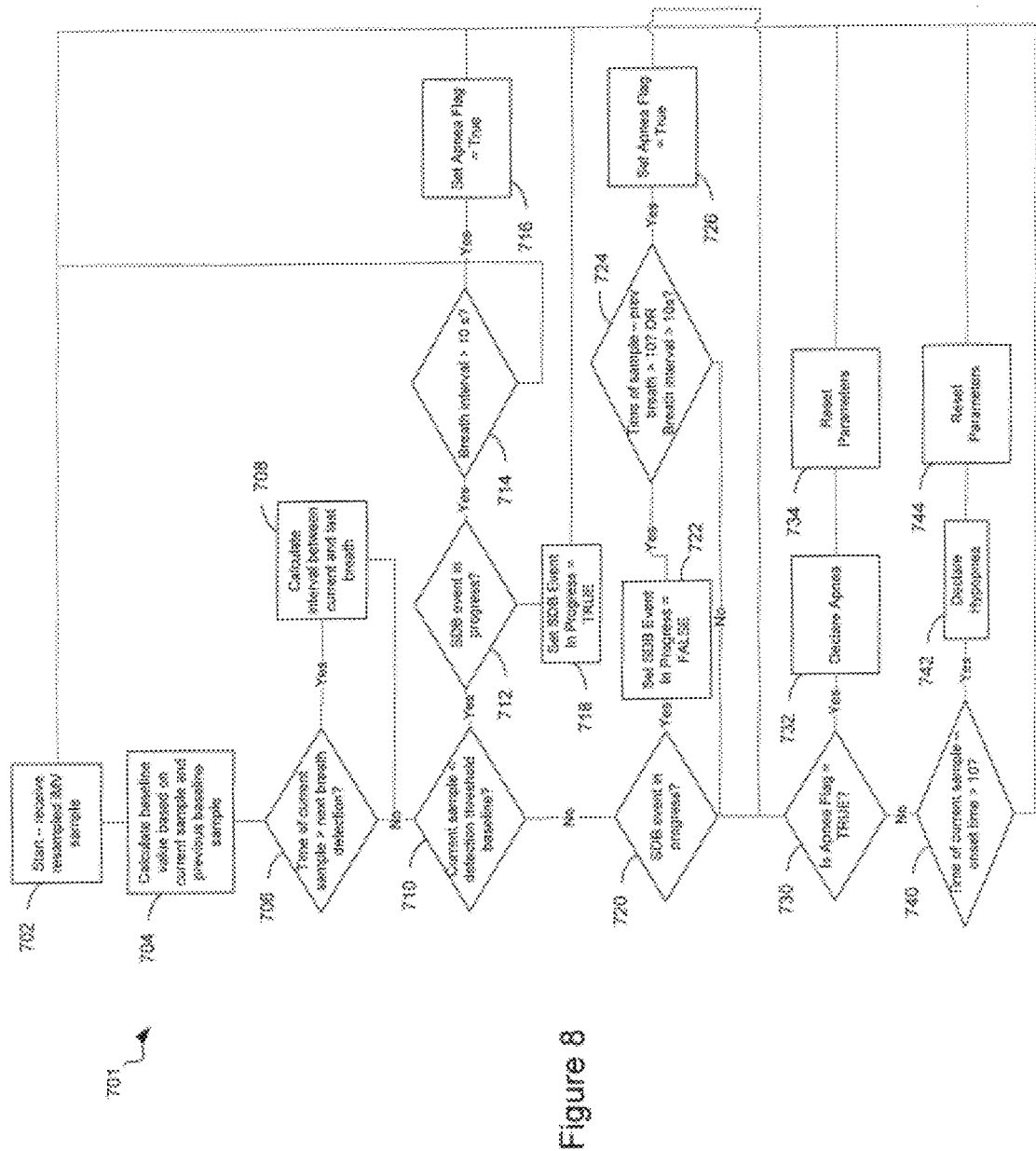
FIG. 8 is a flow diagram showing various processes for implantably computing instantaneous minute ventilation for purposes of detecting disordered breathing in accordance with embodiments of the present invention.

Breathing disorders may be determined using an iMV signal or a resampled iMV signal produced from the impedance signal 100 or other physiologic signal that is modulated by patient respiration (i.e., a surrogate respiration signal). During non-REM sleep, a normal respiration pattern includes regular, rhythmic inspiration—expiration cycles without substantial interruptions. When the iMV signal or resampled iMV signal of the patient's respiration falls below a hypopnea threshold, then a hypopnea event is declared. If the patient's iMV signal or resampled iMV signal value minute ventilation falls further to an apnea threshold, e.g., about 10% of the recent average iMV signal or resampled iMV signal value minute ventilation or other baseline value, an apnea event is declared. FIG. 8, which is described in detail hereinbelow, illustrates processes according to embodiments of the present invention for detecting hypopnea and apnea events.

Figure 6:
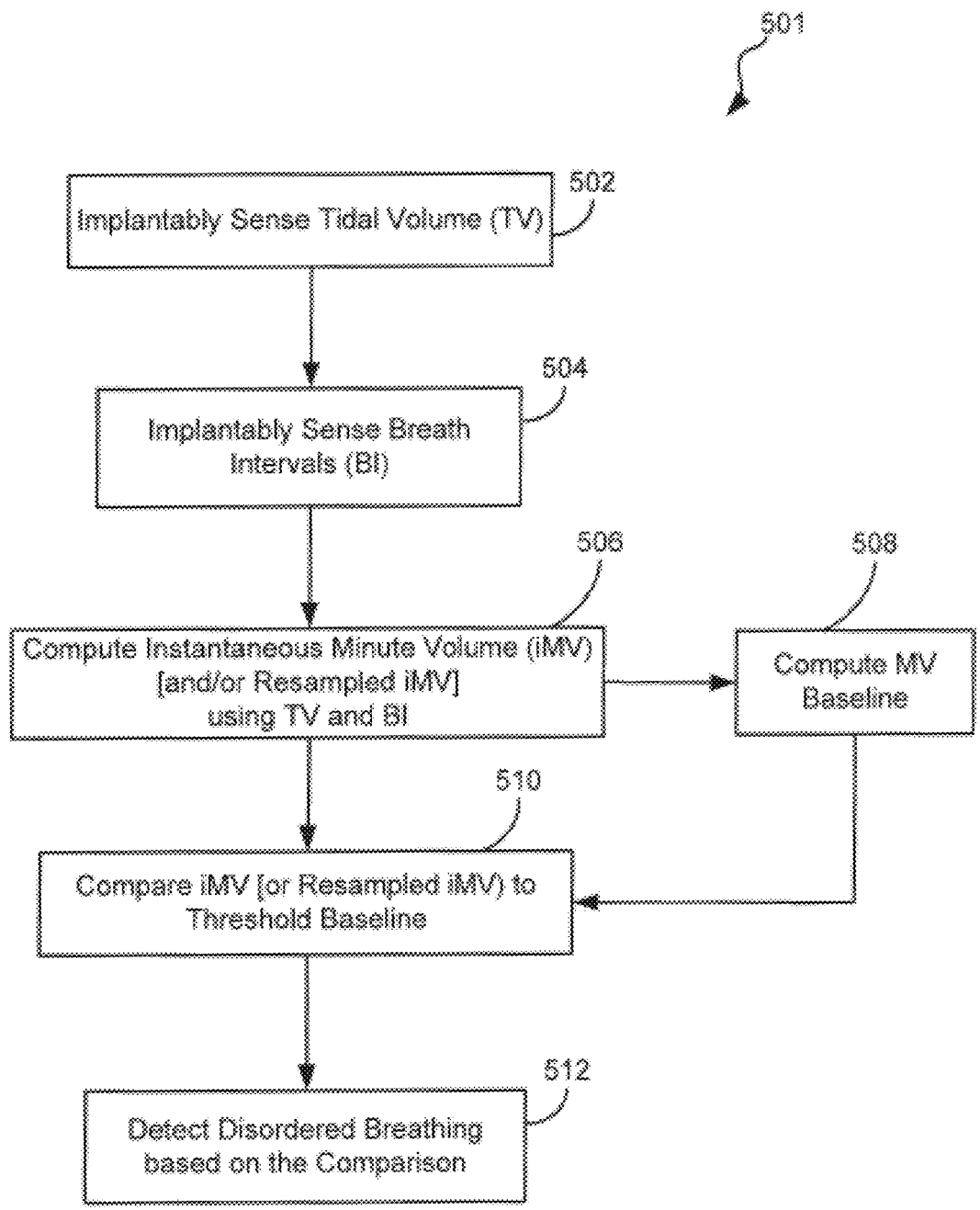
FIG. 6 is a flow diagram showing various processes for implantably computing instantaneous minute ventilation for purposes of detecting disordered breathing in accordance with embodiments of the present invention.

FIG. 6 is a flow diagram showing various processes 501 for implantably computing iMV for purposes of detecting disordered breathing in accordance with embodiments of the present invention. According to FIG. 6, a patient's tidal volume (TVOL) is sensed 502 within the patient, preferably on a breath-by-breath basis. The patient's breath interval (BI) is sensed 504 within the patient, preferably on a breath-by-breath basis. The patient's instantaneous minute ventilation (iMV) is computed 506 using the sensed TVOL and BI signals. An MV baseline is preferably concurrently computed 508, which requires at least two breath intervals. Optionally, the iMV signal may then be interpolated to create a constant sample rate signal (i.e., resampled iMV signal). After the first MV baseline value is computed, the algorithm continues for subsequent breaths by comparing 510 the iMV signal or resampled iMV signal to a threshold baseline. Disordered breathing is detected 512 based on this comparison.

Figure 7:
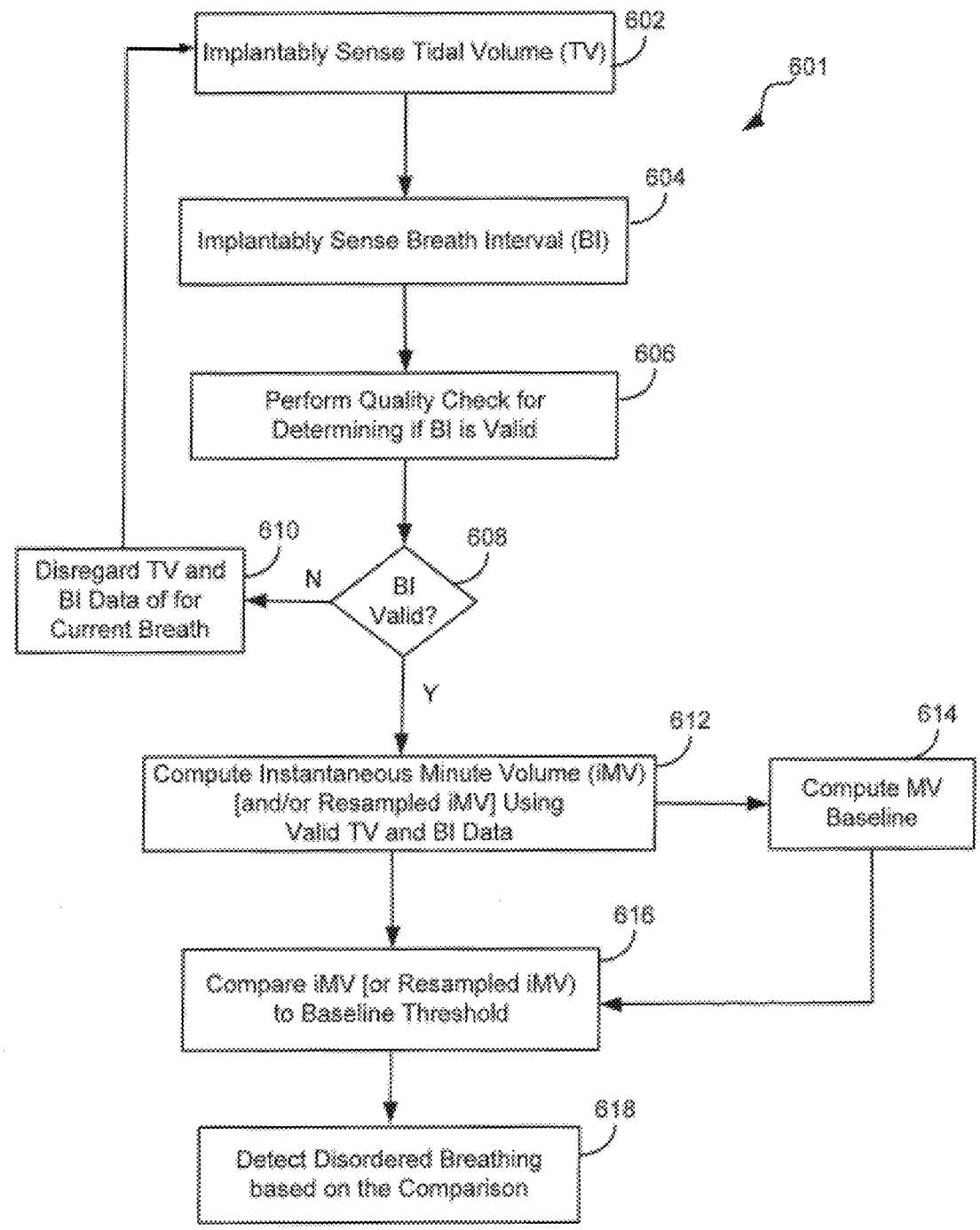
FIG. 7 is a flow diagram showing various processes for implantably computing instantaneous minute ventilation and validating same for purposes of detecting disordered breathing in accordance with embodiments of the present invention.

FIG. 7 is a flow diagram showing various processes 601 for implantably computing instantaneous minute ventilation and validating same for purposes of detecting disordered breathing in accordance with embodiments of the present invention. As is illustrated in FIG. 7, a patient's tidal volume and breath interval are sensed 602, 604 within the patient, preferably on a breath-by-breath basis. A quality check is made 606 for purposes of determining whether the current breath interval is valid. If the current breath interval is not valid, as is tested in block 608, the TVOL and BI data for the current breath are disregarded, and the logic returns to block 602. It is noted that the validation procedure shown in blocks 606-610 can be based on respiratory parameters other than breath interval, such as minute ventilation and tidal volume.

If the current breath interval is valid, then the patient's iMV and/or resampled iMV is computed 612 using the current TVOL and BI signal data. An MV baseline is preferably concurrently computed 614, which requires at least two breath intervals. After the first MV baseline value is computed, the algorithm continues for subsequent breaths by comparing 616 iMV or resampled iMV to a threshold baseline. Disordered breathing is detected 618 based on this comparison.

According to one approach, performing a quality check on a breath interval involves MV sensing circuitry determining if a current breath interval meets predetermined validity criteria. For example, false BI values may be returned during an MV settling time as a result of a noise transition or high voltage event. When a respiration is detected by the MV sensing circuitry, a message is sent to disordered breathing detection circuitry about the current breath interval. This message typically contains a list of parameters about the breath, including parameters indicating whether or not the current breath interval is valid. Only when a good or valid breath is detected by the MV sensing circuitry does the DB detection circuitry continue the baseline calculation and DB detection logic.

For example, it has been observed in clinical trials that a minute ventilation sensor signal may occasionally be too small to detect accurately. Small amplitude MV sensor signals and missed breath detections may generate false positive apnea or hypopnea detections. To mitigate this issue, those periods of time in which MV sensor signal quality is low should be ignored in the analysis.

According to some embodiments, an MV short-term average calculation may be employed that uses a $15/16$ old+$1/16$ new IIR filter to generate a figure of merit. The figure of merit is calculated every 7.5 s and compared to a threshold. Below-threshold respiratory intervals are not counted towards usable analysis time and apnea or hypopnea detections are rejected. Above-threshold respiratory intervals are counted towards usable analysis time and apnea or hypopnea detections are included.

In one approach, a mid-term baseline or MTBL calculation is made that is semi-empirical in its usage. It is formulated by using a "short-term average," where $1/16$ of the short-term average (a type of "MV") is added to $15/16$ of the previous MTBL every 7.5 seconds. This is an exponential type of filter where the MTBL would approach a step change in the short-term average after about 2*16*7.5 seconds. The level of the MTBL under which the determination of an apnea or hypopnea is equivocal can be determined empirically by comparing data from a scored sleep study to the measured MTBL. The level of MTBL is preferably chosen such that by discarding those episodes under this value, the correspondence of the remaining episodes between the sleep study data (i.e., "gold standard") and the impedance based apnea-hypopnea determination is the greatest.

FIG. 8 is a flow diagram showing various processes 701 for implantably computing a patient's resampled iMV for purposes of detecting disordered breathing in accordance with embodiments of the present invention. As is shown in FIG. 8, a resampled iMV sample is received 702. A baseline value is calculated 704 based on the current resampled iMV sample and previous baseline sample(s). If the duration of the current resampled iMV sample is greater than a duration of the next breath, as is tested at block 706, the interval between the current and last breath is calculated 708.

If, at block 706, the duration of the current resampled iMV sample is not greater than the duration of the next breath, then a check is made at block 710 to determine if the current resampled iMV sample is less than the hypopnea detection baseline threshold. If so, a check is made to determine 712 if a sleep disordered breathing (SDB) event is in progress. If an SDB event is not in progress, an SDB Event in Progress flag is set 718 to TRUE, and the logic returns to block 702. If an SDB event is in progress, a check is made 714 to determine if the breath interval is greater than a predetermined duration, such as 10 seconds. If so, then an Apnea Flag is set 716 to TRUE, otherwise the logic returns to block 702.

If, at block 710, it is determined that the current resampled iMV sample is not less than the detection baseline threshold, then a check is made 720 to determine if an SDB event is in progress. If so, then the SDB Event in Progress Flag is set 722 to FALSE. A check is made to determine 724 if the time of the resampled iMV sample minus the previous breath is greater than 10 seconds OR if the breath interval is greater than 10 seconds. In block 724, if the resampled iMV sample falls below threshold, and then rises above threshold, it is necessary to determine if the intervals while the resampled iMV sample was below threshold were sufficiently long for an apnea event. Therefore, a check is made to determine if the length of time between breath intervals was >10 second, or if the time of the current resampled iMV sample and the previous breath was >10 seconds. If this is the case, then this event should be marked as an apnea. If so, the Apnea Flag is set 726 to TRUE and the logic proceeds to block 730, otherwise the logic skips block 726 and proceeds to block 730.

Figure 12:
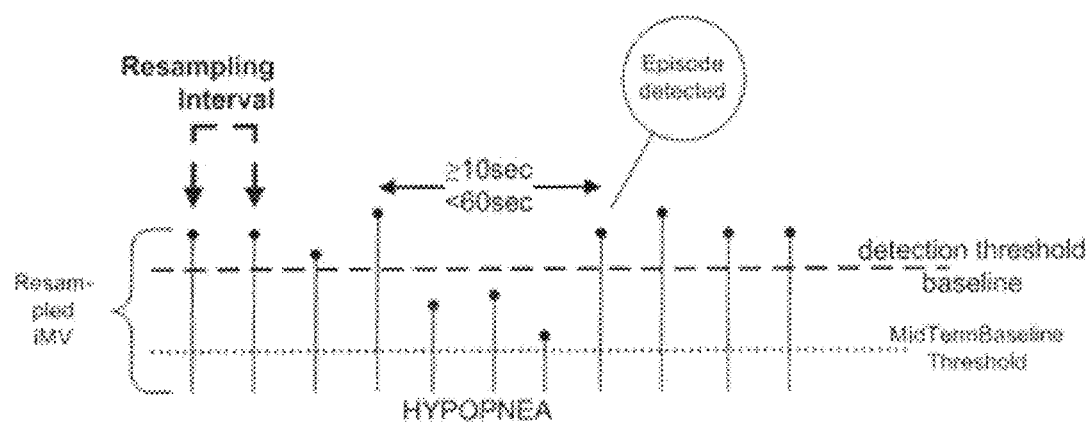
FIGS. 12 and 13 are graphical illustrations of hypopnea and apnea detection results produced by the detection processes depicted in FIG. 8 in accordance with embodiments of the invention.
Figure 13:
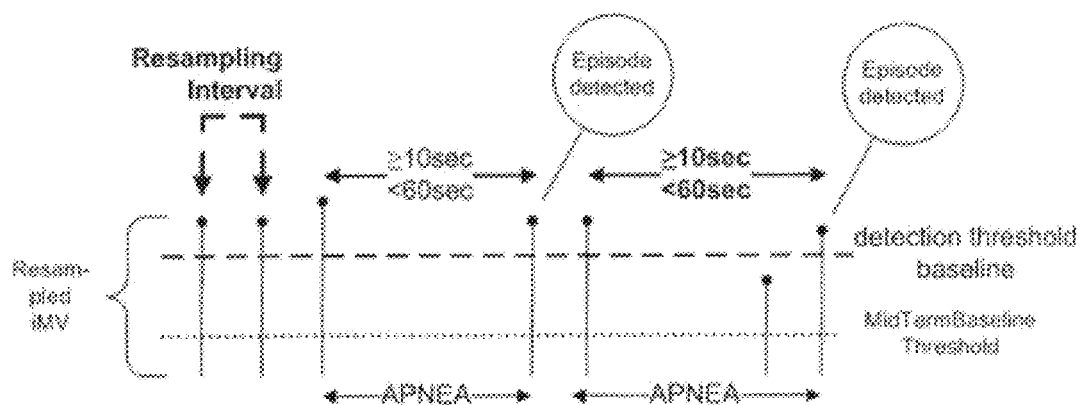

At block 730, a check is made to determine if the Apnea Flag is set to TRUE. If so, an apnea event is declared 732, parameters are reset 734, and logic returns to block 702. If the Apnea Flag is not set to TRUE at block 730, a check is made to determine 740 if the time of the current resampled iMV sample minus the onset time is greater than 10 seconds. In this case, the Apnea Flag was not previously set. Since the resampled iMV sample was below threshold, and at no time was it more than 10 seconds between breaths, a check is made to determine if the time below threshold was >10 seconds. If so, a hypopnea event is declared 742, parameters are reset 744, and the logic returns to block 702. FIGS. 12 and 13 are graphical illustrations of hypopnea and apnea detection results produced by the detection processes depicted in FIG. 8.

Figure 9:
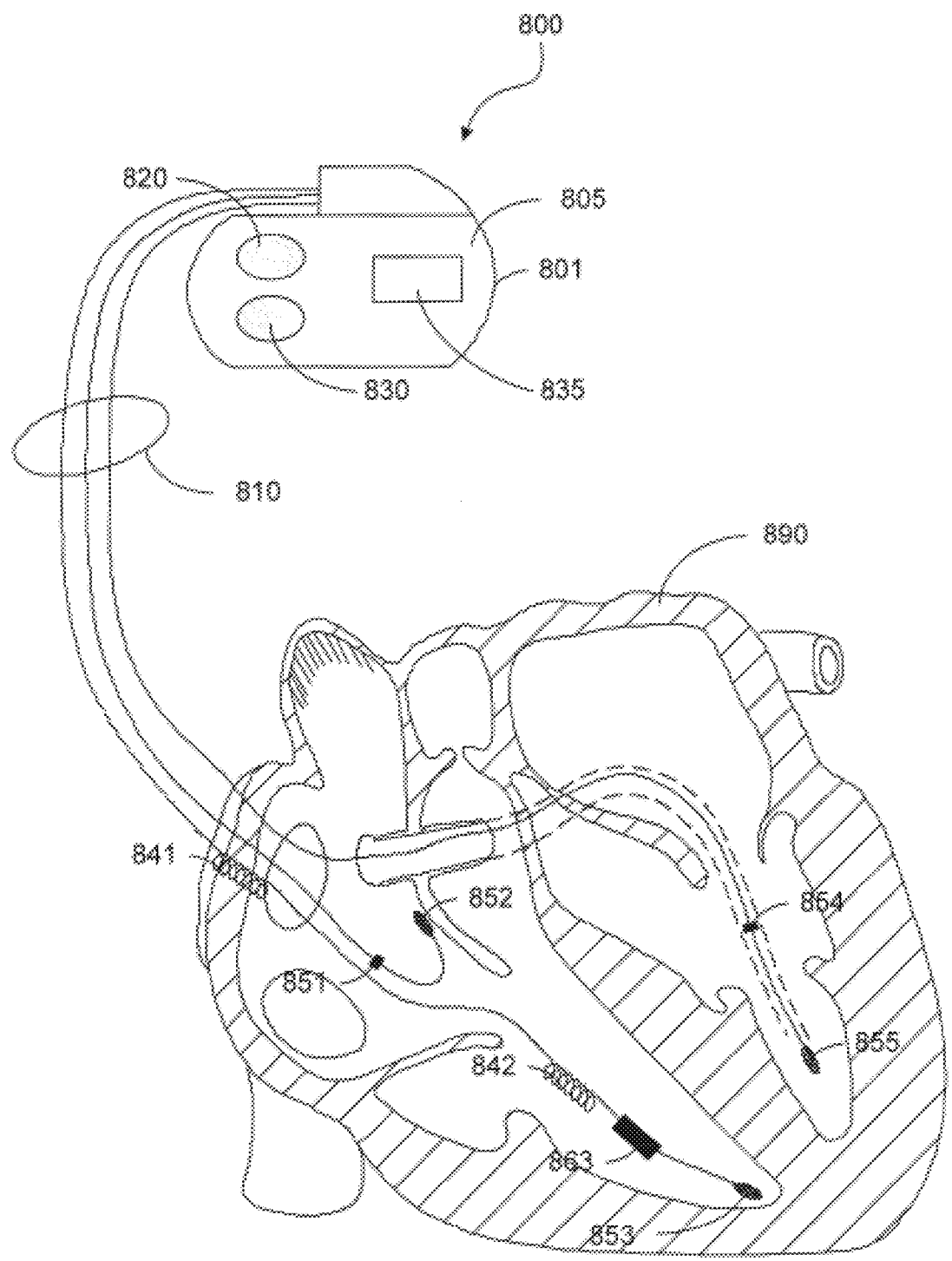
FIG. 9 is an illustration of a cardiac rhythm management system that implements disordered breathing diagnostics in accordance with embodiments of the present invention.

FIG. 9 is an illustration of a cardiac rhythm management system that implements disordered breathing diagnostics in accordance with embodiments of the present invention. The system 800 shown in FIG. 9 may be configured to include circuitry and functionality for sleep disordered breathing detection in accordance with embodiments of the invention. In this illustrative example, disordered breathing diagnostic circuitry 835 is configured as a component of a pulse generator 805 of a cardiac rhythm management device 800. The implantable pulse generator 805 is electrically and physically coupled to an intracardiac lead system 810. The disordered breathing diagnostic circuitry 835 may alternatively be implemented in a variety of implantable monitoring, diagnostic, and/or therapeutic devices, such as an implantable cardiac monitoring device, an implantable drug delivery device, or an implantable neurostimulation device, for example.

Portions of the intracardiac lead system 810 are shown inserted into the patient's heart 890. The intracardiac lead system 810 includes one or more electrodes configured to sense electrical cardiac activity of the heart, deliver electrical stimulation to the heart, sense the patient's transthoracic impedance, and/or sense other physiological parameters, e.g., cardiac chamber pressure or temperature. Portions of the housing 801 of the pulse generator 805 may optionally serve as a can electrode.

Communications circuitry is disposed within the housing 801, facilitating communication between the pulse generator 805 including the disordered breathing diagnostic circuitry 835 and an external device, such as a disordered breathing therapy device, programmer, and/or an advanced patient management (APM) system. The communications circuitry can also facilitate unidirectional or bidirectional communication with one or more implanted, external, cutaneous, or subcutaneous physiologic or non-physiologic sensors, patient-input devices and/or information systems.

The pulse generator 805 may optionally incorporate an electromyogram (EMG) sensor 820 disposed on the housing 801 of the pulse generator 805. The EMG sensor may be configured, for example, to sense myopotentials of the patient's skeletal muscle in the pectoral region. Myopotential sensing may be used in connection with sleep disorders associated with involuntary limb movement.

The pulse generator 805 may further include a sensor configured to detect patient motion. The motion detector may be implemented as an accelerometer positioned in or on the housing 801 of the pulse generator 805. If the motion detector is implemented as an accelerometer, the motion detector may also provide acoustic information, e.g. rales, coughing, S1-S4 heart sounds, cardiac murmurs, and other acoustic information. The lead system 810 of the CRM device 800 may incorporate a transthoracic impedance sensor that may be used to acquire the patient's cardiac output, or other physiological conditions related to the patient's sleep disorder(s). The transthoracic impedance sensor may include, for example, one or more intracardiac electrodes 840, 842, 851-855, 863 positioned in one or more chambers of the heart 890. The intracardiac electrodes 841, 842, 851-855, 861, 863 may be coupled to impedance drive/sense circuitry 830 positioned within the housing of the pulse generator 805.

The impedance signal may also be used to detect the patient's respiration waveform and/or other physiological changes that produce a change in impedance, including pulmonary edema, heart size, cardiac pump function, etc. The respiratory and/or pacemaker therapy may be altered on the basis of the patient's heart condition as sensed by impedance.

In one example, the transthoracic impedance may be used to detect the patient's respiratory waveform, examples of which are shown in FIGS. 1-5. A voltage signal developed at the impedance sense electrode 852, illustrated in FIGS. 1-5, is proportional to the patient's transthoracic impedance and represents the patient's respiration waveform. The transthoracic impedance increases during respiratory inspiration and decreases during respiratory expiration. The transthoracic impedance may be used to determine the amount of air moved in one breath, denoted the tidal volume and/or the amount of air moved per minute, denoted the minute ventilation. A normal "at rest" respiration pattern, e.g., during non-REM sleep, includes regular, rhythmic inspiration expiration cycles without substantial interruptions, as indicated in FIG. 4.

Returning to FIG. 9, the lead system 810 may include one or more cardiac pace/sense electrodes 851-855 positioned in, on, or about one or more heart chambers for sensing electrical signals from the patient's heart 890 and/or delivering pacing pulses to the heart 890. The intracardiac sense/pace electrodes 851-855, such as those illustrated in FIG. 9, may be used to sense and/or pace one or more chambers of the heart, including the left ventricle, the right ventricle, the left atrium and/or the right atrium. The lead system 810 may include one or more defibrillation electrodes 841, 842 for delivering defibrillation/cardioversion shocks to the heart.

The pulse generator 805 may include circuitry for detecting cardiac arrhythmias and/or for controlling pacing or defibrillation therapy in the form of electrical stimulation pulses or shocks delivered to the heart through the lead system 810. Disordered breathing diagnostic circuitry 835 may be housed within the housing 801 of the pulse generator 805. The disordered breathing diagnostic circuitry 835 may be coupled to various sensors, including the transthoracic impedance sensor 830, EMG sensor 820, electroencephalogram (EEG) sensors, cardiac electrogram sensors, nerve activity sensors, and/or other sensors capable of sensing physiological signals useful for disordered breathing detection.

The disordered breathing diagnostic circuitry 835 may be coupled to a sleep disorder detector configured to detect sleep disorders such as disordered breathing, and/or movement disorders. An arousal detector and a sleep disorder detector may be coupled to a processor that may use information from the arousal detector and the sleep disorder detector to associate sleep disorder events with arousal events. The processor may trend the sleep disorder events and/or arousal events, associate the sleep disorder events with arousal events, and/or use the detection of the arousal events and/or the sleep disorder events for a variety of diagnostic purposes. The sleep disorder detector and/or the processor may also be configured as a component of the pulse generator 805 and may be positioned within the pulse generator housing 801. In one embodiment, information about the sleep disorder events and/or arousal events may be used to adjust therapy delivered by the CRM device 800 and/or other therapy device.

For purposes of illustration, and not of limitation, various embodiments of devices implemented in accordance with the present invention are described herein may be implanted under the skin in the chest region of a patient. A patient implantable medical device (PIMD) that implements MV-based disordered breathing detection of the present invention may, for example, be implanted subcutaneously such that all or selected elements of the device are positioned on the patient's front, back, side, or other body locations suitable for sensing cardiac activity and/or delivering cardiac stimulation therapy. It is understood that elements of the PIMD may be located at several different body locations, such as in the chest, abdominal, or subclavian region with electrode elements respectively positioned at different regions near, around, in, or on the heart.

The primary housing (e.g., the active or non-active can) of the PIMD, for example, may be configured for positioning outside of the rib cage at an intercostal or subcostal location, within the abdomen, or in the upper chest region (e.g., subclavian location, such as above the third rib). In one implementation, one or more leads incorporating electrodes may be located in direct contact with the heart, great vessel or coronary vasculature, such as via one or more leads implanted by use of conventional transvenous delivery approaches. In another implementation, one or more electrodes may be located on the primary housing and/or at other locations about, but not in direct contact with the heart, great vessel or coronary vasculature.

In a further implementation, for example, one or more electrode subsystems or electrode arrays may be used to sense cardiac activity and deliver cardiac stimulation energy in a PIMD configuration employing an active can or a configuration employing a non-active can. Electrodes may be situated at anterior and/or posterior locations relative to the heart. Examples of useful electrode locations and features that may be employed in various embodiments of the present invention are described in commonly owned, co-pending U.S. Publication No. 2004/0230230 and U.S. Pat. No. 7,499,750, which are hereby incorporated herein by reference.

Figure 10:
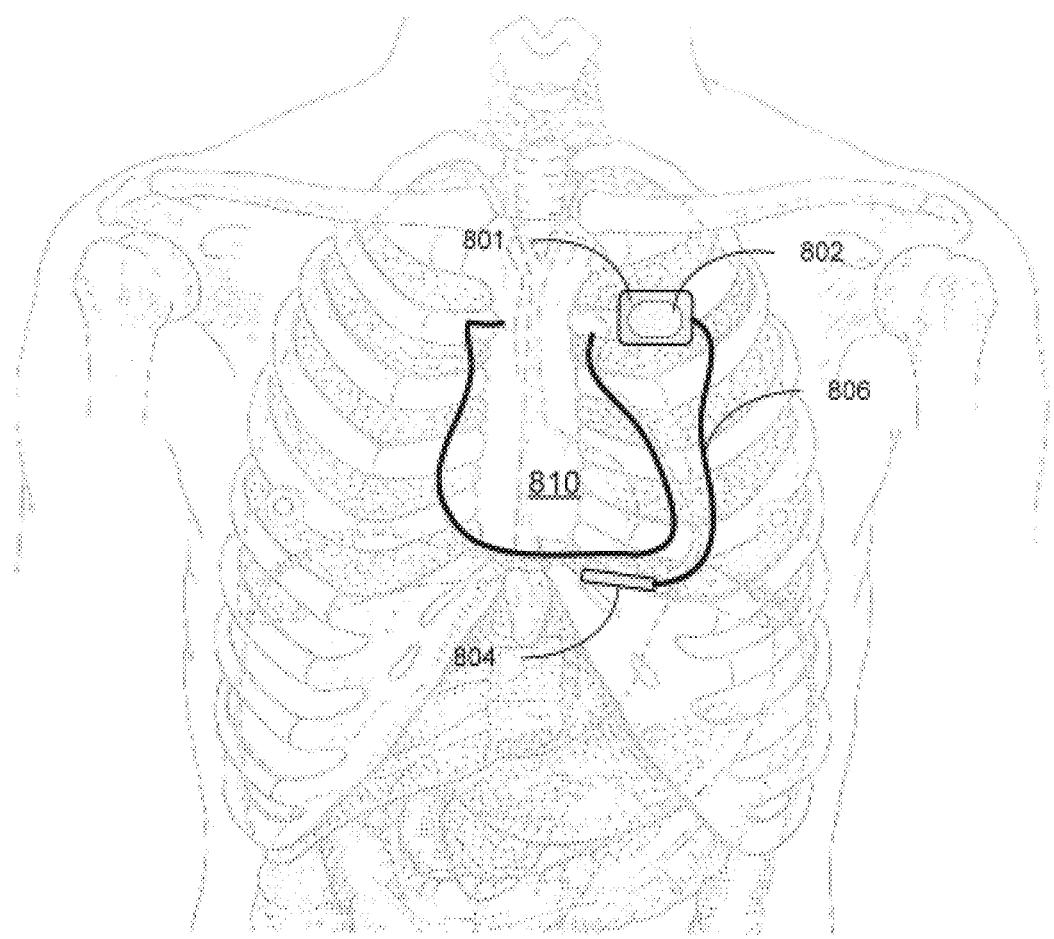
FIG. 10 is an illustration of an implantable medical device including a subcutaneous, non-intrathoracic lead assembly shown implanted outside the ribcage, the implantable medical device implemented to detect disordered breathing in accordance with embodiments of the present invention.

In one configuration, as is illustrated in FIG. 10, electrode subsystems of a PIMD system are arranged about a patient's heart 810. The PIMD system includes a first electrode subsystem, comprising a can electrode 802, and a second electrode subsystem 804 that includes at least two electrodes or at least one multi-element electrode. The second electrode subsystem 804 may include a number of electrodes used for sensing and/or electrical stimulation.

In various configurations, the second electrode subsystem 804 may include a combination of electrodes. The combination of electrodes of the second electrode subsystem 804 may include coil electrodes, tip electrodes, ring electrodes, multi-element coils, spiral coils, spiral coils mounted on non-conductive backing, screen patch electrodes, and other electrode configurations as will be described below. A suitable non-conductive backing material is silicone rubber, for example.

The can electrode 802 is positioned on the housing 801 that encloses the PIMD electronics. The PIMD system shown in FIG. 10 incorporates one or more sensors configured to sense respiration. A sensing element, e.g., electrode, used for respiration sensing may be disposed on housing 801, such that element 802 may be representative of such electrode(s) alone or in combination with a can electrode. Sensing elements used for respiration sensing may be disposed on another component of the PIMD system, such as on lead 806, a lead separate from lead 806, or on the subsystem element 804, which may be representative of such sensing element(s) alone or in combination with a cardiac electrode.

A PIMD of the present invention may be implemented to communicate with a patient management server or network via an appropriate communications interface or an external programmer. A PIMD of the present invention may be used within the structure of an APM system. The advanced patient management system allows physicians to remotely and automatically monitor cardiac and respiratory functions, as well as other patient conditions.

In one example, a PIMD implemented as a cardiac pacemaker, defibrillator, or resynchronization device may be equipped with various telecommunications and information technologies that enable real-time data collection, diagnosis, and treatment of the patient. Various PIMD embodiments described herein may be used in connection with advanced patient management. Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

The components, functionality, and structural configurations depicted herein are intended to provide an understanding of various features and combination of features that may be incorporated in a PIMD. It is understood that a wide variety of PIMDs and other implantable cardiac monitoring and/or stimulation device configurations are contemplated, ranging from relatively sophisticated to relatively simple designs. As such, particular PIMD or cardiac monitoring and/or stimulation device configurations may include particular features as described herein, while other such device configurations may exclude particular features described herein.

Figure 11:
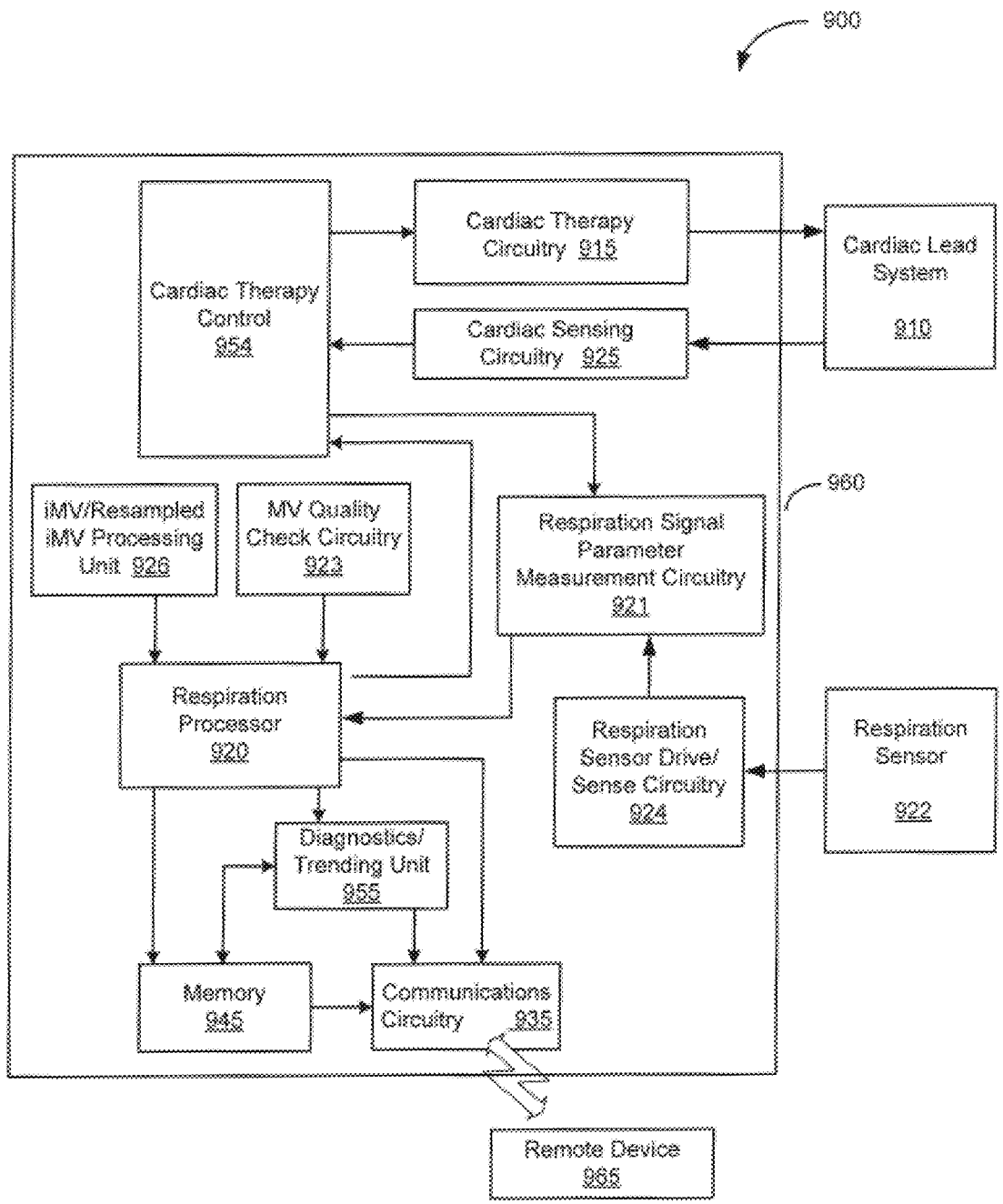
FIG. 11 illustrates a block diagram of a system suitable for implementing the methods of the invention as illustrated, for example, by the processes of FIGS. 6-8 in accordance with embodiments of the invention.

FIG. 11 illustrates a block diagram of a system 900 suitable for implementing the methods of the invention as illustrated, for example, by the processes of FIGS. 6-8. In some embodiments, circuitry for detecting disordered breathing using an MV-based methodology is disposed within the housing of an implantable cardiac rhythm device 960. The cardiac rhythm device 960 includes a cardiac lead system 910 that is electrically coupled to the patient's heart. Electrical signals from the patient's heart are sensed via the lead system 910 by cardiac sensing circuitry 925. The cardiac therapy control circuitry 954 may detect arrhythmic conditions, such as bradyarrhythmia or tachyarrhythmia, based on the sensed cardiac electrical signals. Cardiac therapy control circuitry 954 controls cardiac therapy circuitry 915 which generates electrical stimulation pulses delivered to the heart via the lead system 910 to treat various heart rhythm irregularities. For example, the cardiac therapy circuitry 914 may generate a series of low energy electrical pacing pulses timed to assist the heart in maintaining a hemodynamically appropriate rhythm. The cardiac therapy circuitry 914 may generate high energy shocks delivered to the heart if the cardiac control circuitry 954 detects tachycardia or fibrillation, arrhythmic conditions producing a heart rate that is too fast and possibly lethal.

The system 900 includes a sensor 922 for sensing patient respiration. The sensor may be configured, for example, as intracardiac electrodes used to develop a transthoracic impedance signal which tracks respiration. Respiration sensor drive circuitry 924 provides the necessary drive signals to activate the drive electrodes 922. Response signals are sensed via sense electrodes 922 and are conditioned by the respiration sense circuitry 924.

The respiration drive/sense circuitry 924 generates a respiration signal that is received by the respiration characteristic measurement circuitry 921. The measurement circuitry 921 measures one or more characteristics of the respiration signal. In various embodiments, the characteristic measured may comprise, for example, breath rate, breath interval, tidal volume, or other respiration characteristics. A respiration characteristic may be measured for each breath cycle, e.g., breath rate per cycle or breath interval duration per cycle, or multiple breath cycles may be used in the respiration characteristic measurement, e.g., average tidal volume for X number of breath cycles.

The measurement circuitry 921 may pre-process the respiration signal received from the respiration drive/sense circuitry 924 to remove spurious breath detections. In one scenario, the cardiac therapy control processor 954 provides R-R interval information to the measurement circuitry 921. The measurement circuitry 921 compares breath intervals to filtered R-R interval estimates to identify and remove erroneous breath detections that are due to cardiac activity.

A respiration processor 920 receives the measurements and uses the measurements to compute iMV and/or resampled iMV via processing unit 926 and in a manner discussed hereinabove. A quality check of the breath interval or iMV value is made by the quality check circuitry 923. For example, in one implementation, the measurement circuitry 921 measures TVOL and BI for each breath cycle. The respiration processor 920 and processing unit 926 cooperate to generate iMV and/or resampled iMV and detect disordered breathing using iMV/resampled iMV values relative to a baseline threshold. This data and trending data produced by unit 955 may be stored in memory 945, and/or may be transmitted via communications circuitry 935 to a remote device 965.

A system according to the present invention may include one or more of the features, structures, methods, or combinations thereof described herein. For example, a cardiac monitor, cardiac stimulator, drug pump, neurological monitor and/or therapy device, respiration monitor and/or therapy device, or other type of implantable, partially implantable or patient-external medical device may be implemented to include one or more of the advantageous features and/or processes described above. It is intended that such an implanted, partially implanted or patient external device need not include all of the features described herein, but may be implemented to include selected features that provide for useful structures and/or functionality. Such a device may be implemented to provide a variety of therapeutic or diagnostic functions.

The implementation described in connection with FIG. 11 presumes that measurement of respiration characteristics, estimation of respiration characteristics, determination of respiration metrics and developing respiration trends is performed within an implantable device. In other configurations, some or all of these processes may be performed by the remote device 965, which may comprise a patient-external device, or by two or more implantable or patient-external devices that are communicatively coupled. For example, in one configuration, the implantable device 960 may perform one subset of the functions described above and the remote device 965, which may be a device programmer or an advanced patient management system, may perform another subset of the functions. The remote device 965 typically includes a display for displaying respiration, disordered breathing, and other patient information (e.g., text and graphics).

Various modifications and additions can be made to the preferred embodiments discussed hereinabove without departing from the scope of the present invention. For example, methods and systems of the present invention may be implemented using patient-external devices and sensors, and that the embodiments described herein may be implemented in the context of such patient-external devices and sensors. Accordingly, the scope of the present invention should not be limited by the particular embodiments described above, but should be defined only by the claims set forth below and equivalents thereof.

What is claimed is:

1. A method for detecting disordered breathing implemented by an implantable device and at least in part within a patient, comprising:

the implantable device having a processor, the processor configured to execute instructions for:
   detecting a respiration pattern of a plurality of respiration cycles;
   determining breath intervals (BI) and tidal volume (TVOL) measurements of each of the respiration cycles;
   producing an unevenly sampled instantaneous minute ventilation (iMV) signal using the BI and TVOL measurements;
   producing an evenly sampled iMV signal using the unevenly sampled iMV signal;
   determining if each respiration cycle meets predetermined quality criteria for the iMV based at least in part on a short term average MV signal value, a long term moving average MV signal value, and a predetermined quality threshold; and
   detecting disordered breathing based on a comparison between a baseline threshold and the resampled iMV signal using only respiration cycles that meet the predetermined quality criteria;
   wherein the baseline threshold corresponds to a current midterm baseline threshold, and wherein an updated midterm baseline threshold is periodically calculated using a weighted short term average MV signal value and a weighted previous midterm baseline value; and
   one or more of a cardiac rhythm management device, a drug delivery device, and a neurostimulation device delivering therapy to the patient based on the detected disordered breathing.

2. The method of claim 1, further comprising:
producing, only for each respiration cycle that meets the predetermined quality criteria for purposes of detecting disordered breathing, the iMV signal and the resampled iMV signal;
calculated the updated midterm baseline threshold using only breaths that meet the predetermined quality criteria; and
wherein the predetermined quality criteria comprises a breathing interval quality criterion based on the breathing interval of a current breath and the breathing interval of at least a previous breath, and the tidal volume of at least one previous breath.

3. The method of claim 1, wherein the baseline threshold is computed concurrently with detection of the patient's disordered breathing after detection of at least two respiration cycles.

4. The method of claim 1, wherein producing the iMV signal comprises multiplying instantaneous tidal volume and breath interval, and interpolating the iMV signal to produce a uniformly sampled iMV signal indicative of the resampled iMV signal.

5. The method of claim 1, further comprising determining that the patient is asleep, and performing disordered breathing detection after determining that the patient is asleep.

6. The method of claim 1, wherein at least one of the steps of the method is performed externally of the patient.

7. The method of claim 1, wherein each of the steps processes of the method is performed implantably.

8. The method of claim 1, comprising discriminating between at least two types of disordered breathing.

9. The method of claim 1, comprising computing an apnea/hypopnea index.

10. The method of claim 1, comprising communicating at least some disordered breathing information from a patient-internal location to a patient-external location.

11. An implantable device for detecting disordered breathing at least in part within a patient, comprising:
an implantable housing;
a sensor system disposed in the housing and configured to detect a respiration pattern of a plurality of respiration cycles; and
a processor coupled to the sensor system, the processor configured to execute program instructions to:
determine breath intervals (BI) and tidal volume (TVOL) measurements of each of the respiration cycles,
produce an unevenly sampled instantaneous minute ventilation (iMV) signal using the BI and TVOL measurements,
produce an evenly sampled iMV signal using the unevenly sampled iMV signal,
detect disordered breathing based on a comparison between a baseline threshold and the resampled iMV signal,
determine if each respiration cycle meets predetermined quality criteria for calculating the iMV based at least in part on a weighted short term average MV signal value, a long term moving average MV signal value, and a predetermined threshold, and
produce, only for each respiration cycle that meets the predetermined quality criteria for purposes of detecting disordered breathing, the iMV signal and the resampled iMV signal,
wherein the baseline threshold is calculated using only breaths that meet the predetermined quality criteria and disordered breathing is detected using only breaths that meet the predetermined quality criteria; and
the implantable device is configured to implement one or more of cardiac rhythm management, drug delivery and neurostimulation therapy based on the detected disordered breathing.

12. The device of claim 11, wherein the processor is configured to multiply instantaneous tidal volume and breath interval, and interpolate the iMV signal to produce a uniformly sampled iMV signal indicative of the resampled iMV signal.

13. The device of claim 11, wherein the predetermined quality criteria comprises a breathing interval quality criterion based on the breathing interval of a current breath and the breathing interval of at least a previous breath, and the tidal volume of at least one previous breath.

14. The device of claim 11, wherein the sensor system comprises a sensor configured to sense a physiologic signal that is modulated by patient respiration.

15. The device of claim 11, wherein the sensor system comprises a transthoracic impedance sensor or an inter-thoracic pressure sensor.

16. The device of claim 11, wherein the processor is configured to compute the baseline threshold using an average of the patient's iMV signal samples measured over a predetermined period of time.

17. The device of claim 11, wherein the processor is configured to compute the baseline threshold concurrently with detection of the patient's disordered breathing after detection of at least two respiration cycles meeting the predetermined quality criteria.

18. The device of claim 11, wherein the processor is configured to determine that the patient is asleep and to perform disordered breathing detection after determining that the patient is asleep.

19. The device of claim 11, wherein the processor is configured to communicate one or both of respiration information and disordered breathing detection information to a patient-external device.

20. The device of claim 11, wherein the processor is configured to discriminate between at least two types of disordered breathing.

21. The device of claim 11, wherein the processor is configured to compute an apnea/hypopnea index.

22. A device for detecting disordered breathing implemented at least in part within a patient, comprising:
a sensor configured to detect a respiration pattern of a plurality of respiration cycles;
circuitry for determining breath intervals (BI) and tidal volume (TVOL) measurements of each of the respiration cycles;
means for producing an unevenly sampled instantaneous minute ventilation (iMV) signal using the BI and TVOL measurements;
means for producing an evenly sampled iMV signal (resampled iMV signal) using the unevenly sampled iMV signal;
means for determining if each respiration cycle meets predetermined quality criteria for calculating the iMV by comparing a weighted short term average MV signal value and a longer term moving average MV signal value to a predetermined threshold;
means for producing, only for each respiration cycle that meets the predetermined quality criteria for purposes of detecting disordered breathing, the iMV signal and the resampled iMV signal; and
a detector configured to detect disordered breathing based on a comparison between a baseline threshold and the resampled iMV signal,
wherein the baseline threshold is calculated using only breaths that meet the predetermined quality criteria and disordered breathing is detected using only breaths that meet the predetermined quality criteria.

* * * * *